(12) United States Patent
Vaghchhipawala et al.

(10) Patent No.: US 8,669,417 B2
(45) Date of Patent: Mar. 11, 2014

(54) METHODS AND COMPOSITIONS FOR INCREASING PLANT TRANSFORMATION EFFICIENCY

(75) Inventors: Zarir E. Vaghchhipawala, Madison, WI (US); Kirankumar Mysore, Ardmore, OK (US)

(73) Assignee: The Samuel Roberts Noble Foundation, Inc., Ardmore, OK (US)

( * ) Notice: Subject to any disclaimer, the term of this patent is extended or adjusted under 35 U.S.C. 154(b) by 585 days.

(21) Appl. No.: 12/839,792

(22) Filed: Jul. 20, 2010

(65) Prior Publication Data

US 2011/0016589 A1 Jan. 20, 2011

Related U.S. Application Data

(60) Provisional application No. 61/226,987, filed on Jul. 20, 2009.

(51) Int. Cl.
*C07K 14/415* (2006.01)
*A01H 5/12* (2006.01)
*A01H 5/10* (2006.01)
*A01H 5/00* (2006.01)
*C12N 15/84* (2006.01)

(52) U.S. Cl.
USPC ........... 800/278; 800/285; 800/286; 800/294; 800/320; 800/312; 435/468; 435/469; 435/419

(58) Field of Classification Search
None
See application file for complete search history.

(56) References Cited

U.S. PATENT DOCUMENTS

2007/0155014 A1* 7/2007 Bertolini et al. .............. 435/455
2008/0052790 A1* 2/2008 Kovalchuk et al. ........... 800/278

OTHER PUBLICATIONS

Hadi et al. (Plant Cell Reports (1996) 15:500-505).*
Liizumi et al. (Nucleic Acids Research, 2008, vol. 36, No. 19, 6333-6342).*
Anand et al., "Arabidopsis VIRE2 interacting protein2 is required for agrobacterium T-DNA integration in plants," *Plant Cell*, 19:1695-1708, 2007.
Anand et al., "Current advances in agrobacterium-plant interactions and their implications in agricultural biotechnology," In: Advances in Plant Physiology, Hemantaranjan (Ed.), Scientific Publishers, Jodhpur, India, 8:221-242, 2005.
D'Agostino et al., "TomatEST database: in silico exploitation of EST data to explore expression patterns in tomato species," *Nucleic Acids Res.*, 35:D901-D905, 2007.
Friesner et al., "Ku80- and DNA ligase IV-deficient plants are sensitive to ionizing radiation and defective in T-DNA integration," *Plant J.*, 34:427-440, 2003.
Gelvin et al., "Agrobacterium-mediated plant transformation: the biology behind the "gene-jockeying" tool," *Microbiol. and Mol. Biol. Rev.*, 67(1):16-37, 2003.
GenBank Accession No. AF233528, dated Apr. 10, 2002.
GenBank Accession No. AW945092, dated, May 31, 2000.
Li et al., "Involvement of KU80 in T-DNA integration in plant cells," *PNAS USA*, 102:19231-19236, 2005.
Mysore et al., "Arabidopsis ecotypes and mutants that are recalcitrant to agrobacterium root transformation are susceptible to germ-line transformation," *Plant J.*, 21:9-16, 2000.
Nam et al., "Identification of characterization of T-DNA tagged arabidopsis mutants that are resistant to agrobacterium tumefaciens transformation," *Mol. and Gen. Genet.*, 261:429-438, 1999.
NCBI Accession No. NM_113211, dated Aug. 21, 2009.
Tzfira et al., "Agrobacterium-mediated genetic transformation of plants: biology and biotechnology," *Curr. Opin. Biotechnol.*, 17:147-154, 2006.
West et al., "Arabidopsis DNA ligase IV is induced by γ-irradiation and interacts with an arabidopsis homologue of the double strand break repair protein XRCC," *Plant J.*, 24(1):67-78, 2000.
Weterings et al., "DNA-dependent protein kinase in nonhomologous end joining: a lock with multiple keys?," *J. Cell Biol.*, 179:183-186, 2007.

* cited by examiner

*Primary Examiner* — David T Fox
*Assistant Examiner* — Jared Shapiro
(74) *Attorney, Agent, or Firm* — Dentons US LLP

(57) ABSTRACT

The invention provides methods and compositions for increasing the efficiency of genetic transformation of host cells, including plant cells, and other eukaryotic cells, by reducing the expression of a polypeptide active in a pathway, such as the NHEJ pathway, for repairing damage to the cellular genome. In certain embodiments, the polypeptide is active in repairing double strand breaks (DSB's) of a cellular genome, and may include XRCC4, KU70, KU80, the DNA-activated Protein Kinase (DNA-Pkcs), and ATM. Methods for enhancing the resistance of plant cells to Crown Gall disease are also provided. In another aspect, genetic regulatory elements are provided, including an XRCC4 promoter.

22 Claims, 9 Drawing Sheets

FIG. 2

```
At-XRCC4  265  QYLGFQQPNSVYSFSDALEGSKRLSWTFEKEGTKLEWRWKCKPSDDSKKITVGILDFLME  444
               +YLGFQQP S    F DA  G KRLSWTFEKEGTKLEWRWKC+ S +SKK T  ILDFLM+
Nb-XRCC4   33  KYLGFQQPGSXXGFDDAGSGHKRLSWTFEKEGTKLEWRWKCQLSPNSKKTTADILDFLMD  212

At-XRCC4  445  ANIRLSEEVVNKTRSFEKMRSEAERCLAQGEKLCDEKTEFESATYAKFL  591
               ANIRLS+EVV+KT+SFE++R EAE+CL Q EKL  EK EFESA YAK +
Nb-XRCC4  213  ANIRLSDEVVSKTQSFERLREEAEKCLTQSEKLSKEKEEFESAIYAKVM  359
```

FIG. 3
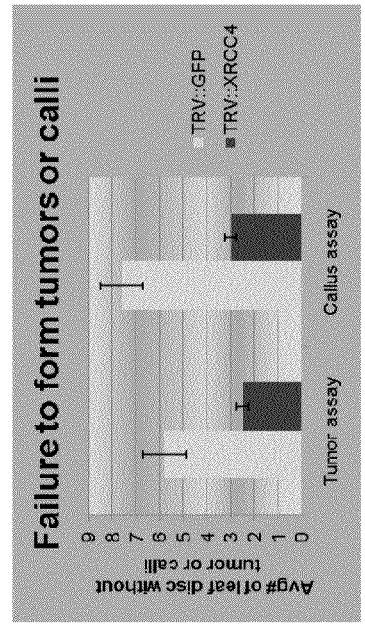
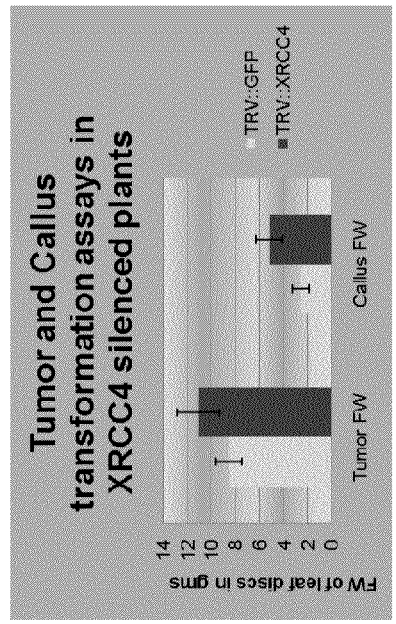
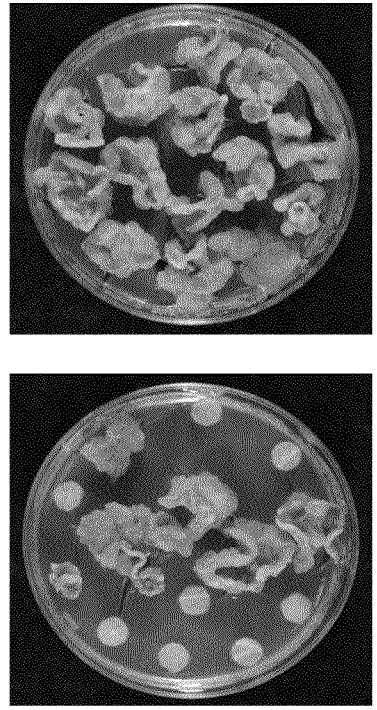
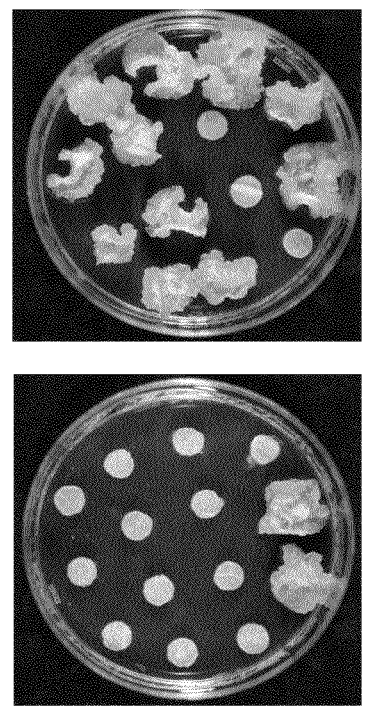
Tumor assay
Callus transformation assay
TRV::*GFP*
TRV::*XRCC4*

FIG. 5
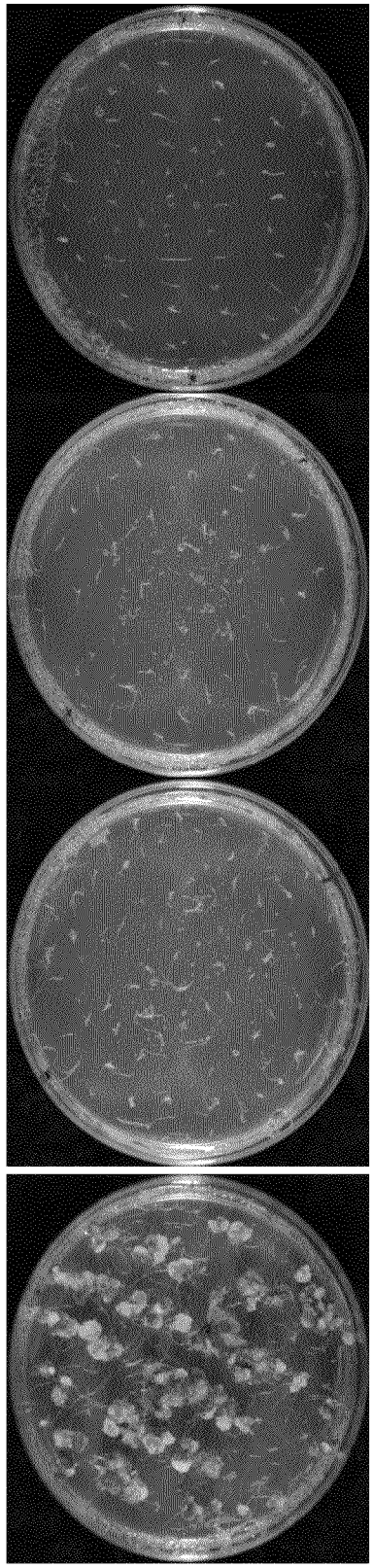
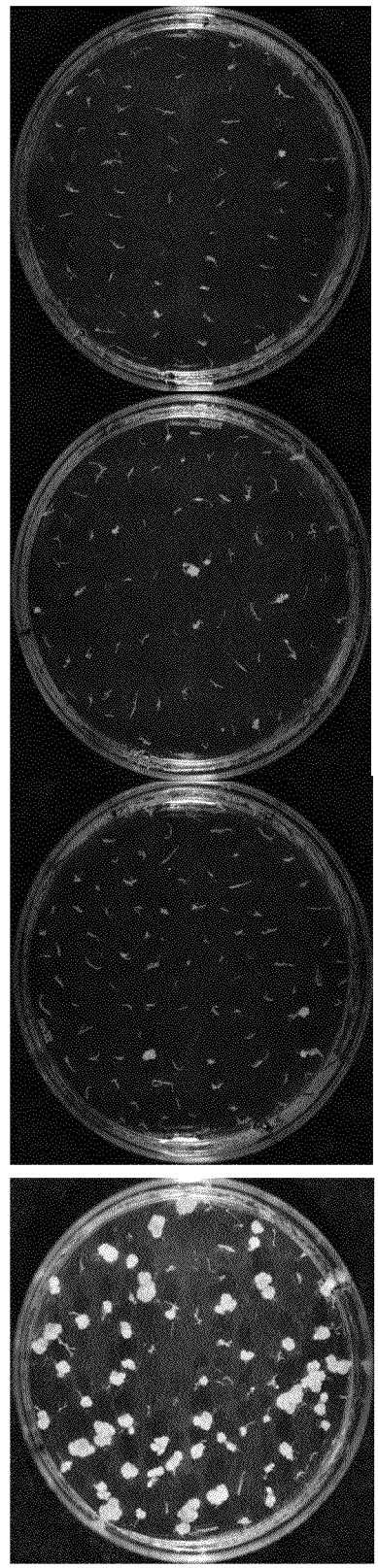

SEQUENCE LISTING

```
<160> NUMBER OF SEQ ID NOS: 15

<210> SEQ ID NO 1
<211> LENGTH: 991
<212> TYPE: DNA
<213> ORGANISM: Arabidopsis thaliana

<400> SEQUENCE: 1
tccacgtaag caaaaccaaa acaaattata gacattatta tgatcggagt tgactcaaaa      60
tcttcgtcga cgacttttat cgaaacaatg gttgaatcgg agaaaacgaa acacacttgt     120
ctccgtctcg aaatctccgg cgccgatcca attttcgtca aaggcacttg gcataattct     180
cgtttcgata tctccgtcac cgatggttcc tcctcttgga tttgcaatgc gacggaggag     240
gaagtggcgg agagagcagc acaatgggac cagcctgtgt cagagtattt aaagctcgcc     300
gagcaatact tagggtttca acaacctaat tcggtctata gtttctccga tgctctagag     360
ggatctaaac ggctctcttg gacgtttgag aaggaaggga ctaaacttga gtggaggtgg     420
aaatgtaaac catcagatga tagcaagaag atcactgttg ggatcttgga ttttcttatg     480
```

-continued

```
gaggctaaca taaggctaag tgaagaagtg gtgaacaaga cgagatcttt tgagaagatg     540
agaagtgaag ctgagagatg tctagcgcaa ggtgaaaaac tctgtgacga aaaaacagag     600
tttgagagtg caacttatgc aaagtttctt tctgttttaa atgcaaagaa ggcaaaactg     660
agagcactaa gggacaaaga agattcagtg agagtagttg aggaggaaga gtcgacagac     720
aaagctgaaa gctttgagag tggaagaagt gatgatgaga agagcgagga agaagcctca     780
aaaaaggcaa caagcagcaa agcccgtggc gggaagagag ctgcacgaag ctaagagatt     840
gccctgccgt gagattttca ggtcagagtt tccattccaa gttttgtcaa actcatagct     900
aggaaaattg tttgtcaaac cttctttggt ttaaaaaaat aatttacaat ttgtattact     960
tctgaaagta aatgcaataa cttagagatg g                                    991
```

<210> SEQ ID NO 2
<211> LENGTH: 264
<212> TYPE: PRT
<213> ORGANISM: Arabidopsis thaliana

<400> SEQUENCE: 2

```
Met Ile Gly Val Asp Ser Lys Ser Ser Thr Thr Phe Ile Glu Thr
  1               5                  10                  15

Met Val Glu Ser Glu Lys Thr Lys His Thr Cys Leu Arg Leu Glu Ile
                 20                  25                  30

Ser Gly Ala Asp Pro Ile Phe Val Lys Gly Thr Trp His Asn Ser Arg
             35                  40                  45

Phe Asp Ile Ser Val Thr Asp Gly Ser Ser Trp Ile Cys Asn Ala
 50                  55                  60

Thr Glu Glu Val Ala Glu Arg Ala Ala Gln Trp Asp Gln Pro Val
 65                  70                  75                  80

Ser Glu Tyr Leu Lys Leu Ala Glu Gln Tyr Leu Gly Phe Gln Gln Pro
                 85                  90                  95

Asn Ser Val Tyr Ser Phe Ser Asp Ala Leu Glu Gly Ser Lys Arg Leu
                100                 105                 110

Ser Trp Thr Phe Glu Lys Glu Gly Thr Lys Leu Glu Trp Arg Trp Lys
            115                 120                 125

Cys Lys Pro Ser Asp Asp Ser Lys Lys Ile Thr Val Gly Ile Leu Asp
            130                 135                 140

Phe Leu Met Glu Ala Asn Ile Arg Leu Ser Glu Glu Val Val Asn Lys
145                 150                 155                 160

Thr Arg Ser Phe Glu Lys Met Arg Ser Glu Ala Glu Arg Cys Leu Ala
                165                 170                 175

Gln Gly Glu Lys Leu Cys Asp Glu Lys Thr Glu Phe Glu Ser Ala Thr
            180                 185                 190

Tyr Ala Lys Phe Leu Ser Val Leu Asn Ala Lys Lys Ala Lys Leu Arg
            195                 200                 205

Ala Leu Arg Asp Lys Glu Asp Ser Val Arg Val Val Glu Glu Glu Glu
        210                 215                 220

Ser Thr Asp Lys Ala Glu Ser Phe Glu Ser Gly Arg Ser Asp Asp Glu
225                 230                 235                 240

Lys Ser Glu Glu Glu Ala Ser Lys Lys Ala Thr Ser Ser Lys Ala Arg
                245                 250                 255

Gly Gly Lys Arg Ala Ala Arg Ser
            260
```

<210> SEQ ID NO 3

```
<211> LENGTH: 770
<212> TYPE: DNA
<213> ORGANISM: Lycopersicon esculentum

<400> SEQUENCE: 3
cactccattg cggtggctgc cgctctagaa ctagtggatc ccccgggctg caggaattcg    60
gcacgaggcc cattattttc ctttgatctt tatagctgtc atggacattt gagaaagaag   120
gaactaccct ggaatggcgg tggaaatgcc aatcgccgtc taatatcaaa aaaactacag   180
ctgatatctt ggacttcctc atggatgcaa atattagact gcctgatgaa gttgtcagta   240
aaactgagtc atttgacagg atgaaggtgg aggcagaaaa atgtttaaca caaagcgaga   300
aactcacctg agagaacgaa gaatttgaat ctgcaatata tgcacagttt cttggagttc   360
tgaacgcaaa gaagataaaa ctcagagaac ttcgcgataa gctctcgaaa caggcaacct   420
ctgttgaaga gccagtagaa gaggacgcac aatatactga cagaactgag acctttgatg   480
aggaaataag cggggaagaa gtggagaatg atgatgttgg cacttcaaaa gatgttccag   540
cccgaacggg tcgtggacgt ggtctaaaga gaaagtaaat gtcttatgat caccatttac   600
aaaattgaat acatccccgt ttttttttg gcctcctttt ttaacaggct tttatgttac   660 tttcctttt ggggaaaat gaccgcaagg gggtttttt ttttacccat gtgggaaatt   720
gggaaatcct acaattattg ggggttttt ctgggagaat ttttcgggaa                770

<210> SEQ ID NO 4
<211> LENGTH: 53
<212> TYPE: DNA
<213> ORGANISM: Artificial sequence
<220> FEATURE:
<223> OTHER INFORMATION: Synthetic primer

<400> SEQUENCE: 4
ggggacaagt ttgtacaaaa aagcaggctc actccattgc ggtggctgcc gct           53

<210> SEQ ID NO 5
<211> LENGTH: 53
<212> TYPE: DNA
<213> ORGANISM: Artificial sequence
<220> FEATURE:
<223> OTHER INFORMATION: synthetic primer

<400> SEQUENCE: 5
ggggaccact ttgtacaaga aagctgggta gtgccaacat catcattctc cac           53

<210> SEQ ID NO 6
<211> LENGTH: 656
<212> TYPE: DNA
<213> ORGANISM: Nicotiana benthamiana

<400> SEQUENCE: 6
accccggttt ctgagtatat taatttgggt gaaagtattt gggatttcaa cagcccggtt    60
cysttwawgg ctttgatgat gctggctctg gccataaaag gctttcctgg acatttgaga   120
aagaaggcac aaagttggaa tggcggtgga atgccaact gtctcctaat agcaagaaaa    180
ctacggcaga catcttggac tttctcatgg atgcaaacat tagacttagt gacgaagttg   240
tcagtaaaac tcaatcattt gagaggctga gagaggaggc tgaaaaatgt ttaacacaaa   300
gcgagaaact cagcaaagag aaagaagaat ttgaatctgc aatatatgca aaggtgatgt   360
tttcagtcca agcactagga tctttttatta atttacggct tggttgcgat atattaatta   420
ttgacctttc tttaacatca tacaatgtat atcctgctac cctttgttgt tggcaatggt   480
```

-continued

| | |
|---|---|
| ttaattaggc ttaggagtag aacatcccaa aagagttggg tttataattg gtcatgactg | 540 |
| tggtcctttt acttccagtt tgtkggagtc ctgaattcaa agaagaaaaa gctcagagaa | 600 |
| cttcgcgata agctctcaaa agagggaacc gctgttcaag agccggtaga agagga | 656 |

<210> SEQ ID NO 7
<211> LENGTH: 53
<212> TYPE: DNA
<213> ORGANISM: Artificial sequence
<220> FEATURE:
<223> OTHER INFORMATION: Synthetic primer

<400> SEQUENCE: 7

| | |
|---|---|
| ggggacaagt ttgtacaaaa aagcaggcta gtgggtcggt cccatttgtc tat | 53 |

<210> SEQ ID NO 8
<211> LENGTH: 53
<212> TYPE: DNA
<213> ORGANISM: Artificial sequence
<220> FEATURE:
<223> OTHER INFORMATION: Synthetic primer

<400> SEQUENCE: 8

| | |
|---|---|
| ggggaccact ttgtacaaga aagctgggtc catctctaag ttattgcatt tac | 53 |

<210> SEQ ID NO 9
<211> LENGTH: 3002
<212> TYPE: DNA
<213> ORGANISM: Arabidopsis thaliana

<400> SEQUENCE: 9

| | |
|---|---|
| actcgtaaac caaagtttct aagatgaaac tagcgtcact ataccacata aatcatttga | 60 |
| attttgagag gtaaaatgta atttataatc tattaagtct tcaccaacat caggatatat | 120 |
| aacaaactca ctaaactaca acaatttggt ttctaatcgt aatattataa tagctttcag | 180 |
| gctagtgtgg ggcaagcttt ttttcctgca attatgcaaa acttctttat atatatgatt | 240 |
| aagtgtgaat tgtgaactat attgaatata atcagacaat cattatgcaa gcacaagggg | 300 |
| acaagatatc aaactattat ttccaaactc caatttaaat ttggctttaa ctatagtatt | 360 |
| tctgtccaat tagtcaaaat acatctgtta tattttgttt atatatacac tccatacaaa | 420 |
| aaaaatatat acatatatca aaatttacaa tctactgact acaatcatta caaaacacac | 480 |
| atgaattaca acatagttca acaatcatca tttaaccaac caataaacta aaaacatttc | 540 |
| aacataaatg atttttattg gtttagaaac gtgattttgt ggactttta gcaaggaatc | 600 |
| aataaataaa ctaaaaaaat aagagaaaat aaaataaaaa taagtgatt atagaaaaga | 660 |
| catgacatcc ttattggcat agcatccaat cttattaatt gctcattgat tttgattatc | 720 |
| ccacacctaa actcttattg aaaaacacat tgcaccaccc tggtttgata tttaattttt | 780 |
| aagataagca tctctcatta tgttaaatta tacctgatat gcccttgttg taagtaagag | 840 |
| tcgaaatcga atcggtgata ggttcaaggg taaaataggg gatttagaaa agaagacgtg | 900 |
| ggatgattga gctgtgtgtg atagaggtta tgcgctgagt ggagtaaaag aaagactatc | 960 |
| caacgaataa gtgggtcggt cccatttgtc tataagagta tagccaaaca ataataattc | 1020 |
| tccaaaaatg gttacagaaa aacaataatt aatttcacaa atatataata atattttata | 1080 |
| ttttgggaga tgtatataga cgtcgtagtt agctaaagtg aattaacaaa tagggtttga | 1140 |
| cgttttctaa tatttgtttt tgtttaattg atatttcttt catccgtgta ttaaaaatga | 1200 |
| tcacaacaac gaatcttttt acaaaatttc cgagcacaaa tgaaacctga ttttgtatca | 1260 |

| | |
|---|---|
| aattattttt ggaaacatga ttttctttca aaatatttta caaaccaaaa agacaactag | 1320 |
| aagtctgaag tctttagcga caaatacatt tgttaattaa gattctgtga catcattaat | 1380 |
| agtttaacat gtaccttata atagtaacca gttattttct tatgctcgaa caatcaaaat | 1440 |
| aaatttgtca atttgccaaa aaaaaaatca acattacaat aagataaatt taaatatgaa | 1500 |
| aatcaactta aaacatgtta atgtttatat gcatatttca ctaaagttaa atctaaaata | 1560 |
| gtatatttac agtgatgatg aacacgattt aataattata cgatatccag ataatgtaga | 1620 |
| ctaagtaaag aaatgaagtg agcacaattg taattttaaa tttaacatgt gaataaattg | 1680 |
| tacaaaaaac atctattgat taatattcga taaattagta atcactataa attaataaaa | 1740 |
| aaatttggtt tctagtcaag tgaatataat atttaacatt atttgataaa ataaataaag | 1800 |
| taataattta ttcaaaaatc ctatagaaat atatggtttc attagtatca taaactaaga | 1860 |
| attgtataaa cttattaata tcaatatatg taagaaaatt tagtaaaata tgattttagt | 1920 |
| attgtttggt tttttacgca gagttcaatt atattatttt actacatcaa ttttttttgt | 1980 |
| attgttttgc agagtttagt tatatgaatt gtatcctcat cctgtgtgaa aactctagaa | 2040 |
| attgtgtaac cacatccttc agctttctcc tcaattgatc cgttcaaatt atgtattaat | 2100 |
| gatgtagctg ctttaattga agtcctaaca atctacaccc caaattctca atgatatgtt | 2160 |
| tgggattgta gttggggatg gacgaaggcc aacccgctgc tccaatcata gcactacgaa | 2220 |
| tggtggaaat gtcaagaata aaccactcgg gctcaatatc gtccacattc tcattaagat | 2280 |
| aacttaatag gtcgtcatcg tctttaagaa acaagactct agttattgat gagcgactgt | 2340 |
| taatttatag aagttttact tatttttaatt ttacattata cataaaaaaa atcacgtcat | 2400 |
| tgtataaaat ccactaaggc gcgacctgaa taaactttag aaaaaatttc aaatccgtat | 2460 |
| aactgcattt cgtctcattc acagttgcat gaactcttat catacgattg tgccatgcca | 2520 |
| tattaacatc gtttatcatc caacaatagt ggtggagtta ctttcttatt gagttcaata | 2580 |
| tactaaaaag gaaaacacat aatataattt tttcttttaa aaggcatttt tattattata | 2640 |
| tgtatattat tagaaaaaag tatgattaaa aaaattaaaa agaaatgtaa gtaacaacat | 2700 |
| ttaacggatt ttttatttat taaagataag cttcggttag gatacaaaat acaaagattt | 2760 |
| gccaaactaa tttagatatt cttcaatctt ttgatgagct tcaaagtaat aattactaat | 2820 |
| taatttactg aatgaaaaca gtaatttgtt aatttttaat tacttgtgat aaaaaaataa | 2880 |
| aaaaaaatta ataattactt aaattgtcta tatgtaatgg gagttttttt tttttaacaa | 2940 |
| cttcttttaa gtaaaatcac taaatatatt ttaaaaaaaa caataccgaa gctgactcag | 3000 |
| ca | 3002 |

<210> SEQ ID NO 10
<211> LENGTH: 54
<212> TYPE: DNA
<213> ORGANISM: Artificial sequence
<220> FEATURE:
<223> OTHER INFORMATION: Synthetic primer

<400> SEQUENCE: 10

| | |
|---|---|
| ggggacaagt ttgtacaaaa aagcaggctg aagtgatgat gagaagagcg agga | 54 |

<210> SEQ ID NO 11
<211> LENGTH: 53
<212> TYPE: DNA
<213> ORGANISM: Artificial Sequence
<220> FEATURE:
<223> OTHER INFORMATION: Synthetic primer

<400> SEQUENCE: 11 gggaccact ttgtacaaga aagctgggtc catctctaag ttattgcatt tac        53

<210> SEQ ID NO 12
<211> LENGTH: 22
<212> TYPE: DNA
<213> ORGANISM: Artificial Sequence
<220> FEATURE:
<223> OTHER INFORMATION: Synthetic primer

<400> SEQUENCE: 12
ggcacttggc ataattctcg tt        22

<210> SEQ ID NO 13
<211> LENGTH: 22
<212> TYPE: DNA
<213> ORGANISM: Artificial Sequence
<220> FEATURE:
<223> OTHER INFORMATION: Synthetic primer

<400> SEQUENCE: 13
tcgcattgca aatccaagag ga        22

<210> SEQ ID NO 14
<211> LENGTH: 109
<212> TYPE: PRT
<213> ORGANISM: Arabidopsis thaliana

<400> SEQUENCE: 14

Gln Tyr Leu Gly Phe Gln Gln Pro Asn Ser Val Tyr Ser Phe Ser Asp
1               5                   10                  15

Ala Leu Glu Gly Ser Lys Arg Leu Ser Trp Thr Phe Glu Lys Glu Gly
            20                  25                  30

Thr Lys Leu Glu Trp Arg Trp Lys Cys Lys Pro Ser Asp Asp Ser Lys
        35                  40                  45

Lys Ile Thr Val Gly Ile Leu Asp Phe Leu Met Glu Ala Asn Ile Arg
    50                  55                  60

Leu Ser Glu Glu Val Val Asn Lys Thr Arg Ser Phe Lys Met Arg
65                  70                  75                  80

Ser Glu Ala Glu Arg Cys Leu Ala Gln Gly Glu Lys Leu Cys Asp Glu
                85                  90                  95

Lys Thr Glu Phe Glu Ser Ala Thr Tyr Ala Lys Phe Leu
            100                 105

<210> SEQ ID NO 15
<211> LENGTH: 109
<212> TYPE: PRT
<213> ORGANISM: Nicotiana benthamiana
<220> FEATURE:
<221> NAME/KEY: misc_feature
<222> LOCATION: (11)..(12)
<223> OTHER INFORMATION: Xaa can be any naturally occurring amino acid

<400> SEQUENCE: 15

Lys Tyr Leu Gly Phe Gln Gln Pro Gly Ser Xaa Xaa Gly Phe Asp Asp
1               5                   10                  15

Ala Gly Ser Gly His Lys Arg Leu Ser Trp Thr Phe Glu Lys Glu Gly
            20                  25                  30

Thr Lys Leu Glu Trp Arg Trp Lys Cys Gln Leu Ser Pro Asn Ser Lys
        35                  40                  45

Lys Thr Thr Ala Asp Ile Leu Asp Phe Leu Met Asp Ala Asn Ile Arg
    50                  55                  60

```
Leu Ser Asp Glu Val Val Ser Lys Thr Gln Ser Phe Glu Arg Leu Arg
 65                  70                  75                  80

Glu Glu Ala Glu Lys Cys Leu Thr Gln Ser Glu Lys Leu Ser Lys Glu
                 85                  90                  95

Lys Glu Glu Phe Glu Ser Ala Ile Tyr Ala Lys Val Met
                100                 105
```

METHODS AND COMPOSITIONS FOR INCREASING PLANT TRANSFORMATION EFFICIENCY

This application claims the priority of U.S. Provisional Application Ser. No. 61/226,987, filed Jul. 20, 2009, the entire disclosure of which is incorporated herein by reference.

This invention was made with Government support under Grant No. 0445799 awarded by the U.S. National Science Foundation. The Government has certain rights in the invention.

BACKGROUND OF THE INVENTION

1. Field of the Invention

The present invention relates generally to the field of molecular biology. More specifically, the invention relates to methods and compositions for increasing the efficiency of cell transformation.

2. Description of the Related Art

Methods for stably integrating exogenous DNA into a eukaryotic cellular genome typically rely on the presence of one or more breaks in the chromosome as sites for integration. *Agrobacterium tumefaciens* has been used as a transformation agent due to its natural ability to transfer a fragment of its genome known as the T-DNA into a host plant cell's genome. Other members of the Rhizobiaceae, besides *Agrobacterium*, have also been shown to be capable of transferring T-DNA to host cell genomes (e.g. Broothaerts et al., 2006), and T-DNA transfer to non-plant cells has also been noted (e.g. Bundock et al., 1995). This T-DNA traverses through the cell cytoplasm and into the nucleus as a nucleo-protein complex, interacting with several host proteins along the way, and finally is integrated into the host genome at random sites via double strand breaks (DSBs) in the host DNA (Anand and Mysore, 2005; Gelvin, 2003; Tzfira and Citovsky, 2006).

The mechanism utilized by *A. tumefaciens* and related species to transfer T-DNA into plant cells, and other cells thus allows introduction of engineered DNA, for instance comprising a transgene of interest, into cells. *Agrobacterium* sp., including *A. tumefaciens*, are also known as soil borne phytopathogenic bacteria that cause crown gall disease in plants.

SUMMARY OF THE INVENTION

In one aspect, the invention provides a recombinant vector comprising a polynucleotide sequence selected from the group consisting of: (a) a nucleic acid comprising the sequence of SEQ ID NO:6; (b) a nucleic acid hybridizing to SEQ ID NO:6 under high stringency conditions; (c) a nucleic acid sequence encoding a protein with XRCC4 activity and encoded by a sequence with at least 85% sequence identity to SEQ ID NO:6; and (d) a nucleic acid sequence complementary to the nucleic acid sequences of (a), (b), or (c), wherein the polynucleotide sequence is operably linked to a heterologous promoter. In one embodiment, the recombinant vector comprises a heterologous promoter which is functional in a plant cell.

In another aspect, the invention provides a transgenic plant, or a part thereof, transformed with a construct comprising polynucleotide sequence encoding a nucleotide sequence that suppresses expression of a gene encoding a component of a DNA-repair pathway operably linked to a heterologous promoter functional in the plant or part thereof, wherein the plant or part thereof exhibits increased transformability relative to an otherwise isogenic plant or part thereof lacking the polynucleotide sequence. In certain embodiments the plant is a monocotyledonous plant or a dicotyledonous plant. In certain embodiments, a cell of the plant is provided; in other embodiments, a seed of such a plant is provided, wherein the seed comprises the polynucleotide sequence.

In yet another aspect, there is provided a method for increasing the efficiency of transformation of a cell with a selected DNA, comprising: down-regulating the expression of a gene in a DNA-repair pathway in the cell and transforming the cell the with a selected DNA. In certain embodiments, the DNA-repair pathway is the NHEJ pathway. In particular embodiments, the gene encodes a polypeptide that is active in repair of double strand breaks (DSB) in a cell genome. In yet other embodiments, the gene encodes a polypeptide with XRCC4, KU70, KU80, ATM, or DNA-PKc activity. In a particular embodiment, the gene encodes an XRCC4 polypeptide.

The invention further provides such a cell in which expression of a gene in a DNA-repair pathway is down-regulated, selected from the group consisting of: a plant cell, an animal cell, an insect cell, and a fungal cell. In certain embodiments, the invention provides a method wherein transforming the cell comprises contacting the cell with an *Agrobacterium* cell, or a cell of another member of the Rhizobacteriaceae that comprises the selected DNA. A method wherein the cell is transformed with the selected DNA simultaneously with, or subsequent to, transforming the cell with a sequence that down-regulates the expression of a gene in a DNA-repair pathway is also provided. In a particular embodiment the selected DNA comprises a marker gene. In some embodiments, the gene in the DNA-repair pathway is stably down-regulated; in other embodiments, the gene in the DNA-repair pathway is transiently down-regulated.

In certain embodiments, the cell is a plant cell, such as a dicot cell. In particular embodiments, the cell is a cotton, soybean, rapeseed, sunflower, tobacco, sugarbeet, or alfalfa cell. Alternatively, in other embodiments, the plant cell is a monocot cell, such as a corn, rice, wheat, sorghum, barley, oat, switchgrass, or turfgrass cell. In yet other embodiments, the host cell is a fungal cell.

In other embodiments, a method provided by the invention comprises treating the cell with a DNA damaging agent before or during transformation. In some embodiments the DNA damaging agent induces double strand breaks in the cell genome; in particular embodiments the DNA damaging agent is bleomycin.

In another aspect, the invention provides a method of transforming a cell comprising a) obtaining a cell that expresses a polynucleotide sequence that down-regulates a gene of a DNA-repair pathway in a host cell susceptible to *Agrobacterium*-mediated transformation; and b) transforming the host cell with a selected DNA by *Agrobacterium*-mediated transformation, wherein the efficiency of transformation is increased relative to a cell of the same genotype not expressing the polynucleotide sequence. In some embodiments the host cell is a plant cell, such as a dicot cell. In particular embodiments the dicot cell is a cotton, soybean, rapeseed, sunflower, tobacco, sugarbeet, or alfalfa cell. In other embodiments the plant cell is a monocot cell, such as a corn, rice, wheat, sorghum, barley, oat, switchgrass, or turfgrass cell. In other embodiments the host cell is an insect, human or fungal cell.

In yet another aspect, the invention provides an isolated polynucleotide molecule comprising a polynucleotide sequence selected from the group consisting of: a) a polynucleotide sequence comprising the nucleic acid sequence of SEQ ID NO:9; b) a polynucleotide sequence having at least about 70% sequence identity to the sequence of SEQ ID NO:9 that is capable of regulating transcription of an operably linked transcribable polynucleotide molecule; and c) a fragment of the polynucleotide sequence of a) or b), capable of regulating transcription of an operably linked transcribable polynucleotide molecule. In some embodiments, the recombinant nucleic acid construct comprising the isolated polynucleotide molecule is operably linked to a heterologous transcribable polynucleotide molecule.

In yet another aspect, a method is provided for controlling Crown Gall disease in a plant comprising expressing a gene encoding a polypeptide of a DNA repair pathway in a plant cell. In particular embodiments the gene encodes a polypeptide with XRCC4, KU70, KU80, ATM, or DNA-PKc activity.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein:

FIG. 2. Partial BLAST alignment of *A. thaliana* (SEQ ID NO:14) and *N. benthamiana* (SEQ ID NO:15) XRCC4 predicted polypeptide sequences.

FIG. 3. Tumor and callus transformation assays on XRCC4-silenced *N. benthamiana* plants.

FIG. 5. Reduction in root transformation due to At-XRCC4 over-expression.

DESCRIPTION OF SEQUENCES

Figure 1:
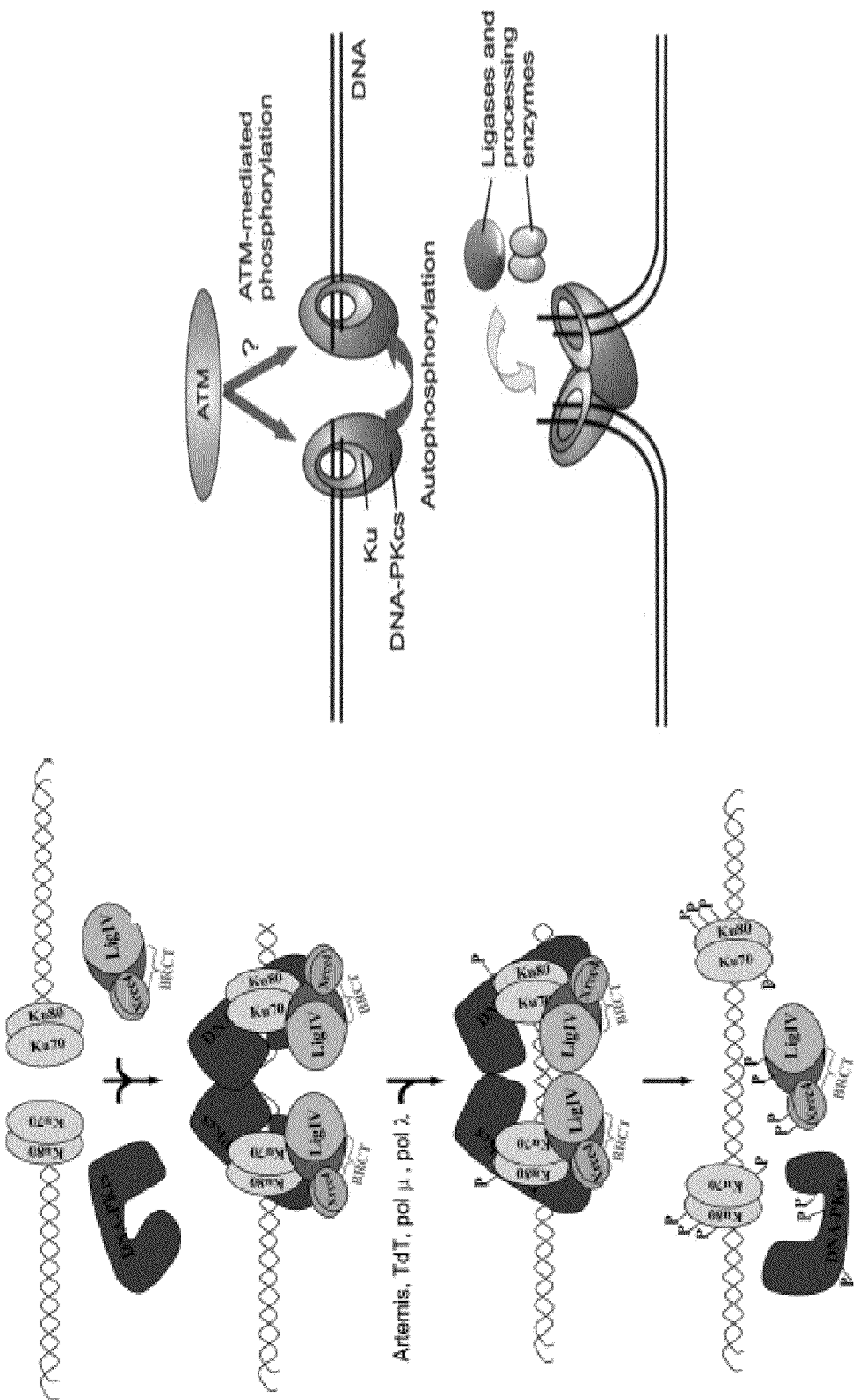
FIG. 1. DNA-repair (NHEJ) pathway components (Weterings & Chen, 2007).

SEQ ID NO:1 Predicted *Arabidopsis thaliana* XRCC4-encoding sequence.

SEQ ID NO:2 Predicted *Arabidopsis thaliana* XRCC4 polypeptide sequence.
SEQ ID NO:3 Tomato XRCC4-related EST sequence.
SEQ ID NO:4 LeXR4-B1 synthetic primer.
SEQ ID NO:5 LeXR4-B2 synthetic primer.
SEQ ID NO:6 *N. benthamiana* XRCC4 sequence.
SEQ ID NO:7 XR4AttB1 synthetic primer.
SEQ ID NO:8 XR4AttB2-R synthetic primer.
SEQ ID NO:9 AtXRCC4 promoter sequence.
SEQ ID NO:10 XR4i-B1F synthetic primer.
SEQ ID NO:11 XR4AttB2-R synthetic primer.
SEQ ID NO:12 XR4 RT-F synthetic primer.
SEQ ID NO:13 XR4 RT-R synthetic primer.
SEQ ID NO:14 Partial *A. thaliana* XRCC4 polypeptide sequence.
SEQ ID NO:15 Partial *N. benthamiana* XRCC4 polypeptide sequence.

DETAILED DESCRIPTION OF THE INVENTION

The invention provides methods and compositions for increasing transformation efficiency involving down-regulating the expression of a gene in a DNA-repair pathway in a cell. In certain embodiments, the methods surprisingly improve the efficiency of *Agrobacterium*-mediated and other Rhizobiaceae-mediated transformation protocols, as well as still other methods for cell transformation. The described methods and compositions are thus useful in enhancing gene transfer to host cells, including plant cells.

In one aspect, the invention provides methods involving down-regulating the non-homologous end-joining ("NHEJ") pathway for DNA repair to surprisingly obtain an increase in transformation efficiency. The invention therefore provides an expression cassette comprising a nucleotide sequence that down-regulates the expression of a gene in a DNA-repair pathway of a cell, operably linked to a promoter which directs expression of the nucleotide sequence in the host cell. In one embodiment, a gene of a DNA-repair pathway down-regulated in accordance with the invention may be one or more of XRCC4, KU70, KU80, ATM or DNA-PKc. In particular embodiments, the host cell is a plant cell, and the expression cassette may be a plant expression cassette. In other embodiments, the cell may be another eukaryotic cell such as a fungal cell, insect cell, or animal cell such as a mammalian cell.

In another aspect the invention provides methods for increasing the efficiency of DNA transfer to a cell, such as *Agrobacterium*-mediated (or other Rhizobiaceae-mediated) gene transfer. The method comprises, in one embodiment, the steps of introducing into a host cell a nucleotide sequence that down-regulates the expression of a gene in DNA-repair pathway, such as the NHEJ pathway, operably linked to a promoter that directs expression of the nucleotide sequence in the host cell. The host cell may include a plant, fungal, insect, or animal cell. In particular embodiments the host cell is a plant cell.

In one embodiment of the invention, transformation efficiency may be improved for the transformation of a monocot plant cell, for instance, a cell of a member of the Poaceae, including corn, wheat, rice, sorghum, sugar cane, rye, oat, barley, turfgrass, switchgrass, or millet, among others. In another embodiment, the plant cell may be a dicot plant cell, for instance a cell derived from a legume such as alfalfa, common bean, or soybean, or other dicot plant including cotton, tobacco, rapeseed, sunflower, sugar beet, among others. Such plants may be susceptible to infection and T-DNA transfer by Agrobacteria or other Rhizobacteria, although other methods for introduction of an exogenous nucleic acid sequence into a host cell are also contemplated.

Thus, methods for increasing the efficiency of gene transfer, such as *Agrobacterium*-mediated gene transfer, are provided. The methods provided by the invention may comprise, in one embodiment, the steps of: obtaining a host cell the genome of which has been modified relative to a wild type cell such that the function (expression) of a gene that acts in a DNA-repair pathway is down-regulated, and (b) transforming the host cell with a selected nucleic acid sequence, wherein the efficiency by which the host cell is transformed is increased relative to an otherwise isogenic cell in which the gene that acts in a DNA-repair pathway has not been down-regulated. In one embodiment, the gene that acts in a DNA-repair pathway may be down-regulated by expressing in the cell a nucleotide sequence that suppresses the expression of the gene. In some embodiments, the nucleotide sequence that suppresses expression of a gene encoding a polypeptide that acts in a DNA-repair pathway may be introduced simultaneously, or before, transforming the host cell with a second exogenous nucleic acid sequence. Suppression of expression of a gene may be accomplished by any method known in the art, for instance via RNAi-mediated suppression and VIGS, among other approaches.

In particular embodiments, the host cell is a plant cell and the second exogenous nucleic acid sequence alters an agronomically useful phenotype selected from the group consisting of: a selectable or screenable marker, herbicide tolerance, increased yield, modified lignin content, altered cellulose or other carbohydrate content, altered metabolite levels, altered oil levels, altered starch levels, increased tolerance to a biotic stress (e.g., resistance or tolerance to insects, fungi, viruses, nematodes, or other pathogen), and increased tolerance toward an abiotic stress (e.g., drought, or cold), among others.

In certain embodiments, transforming the host cell comprises use of an *Agrobacterium* transformation vector, including the contacting of a host cell with an *Agrobacterium* cell or cell of another member of the Rhizobacteriaceae. These steps may be performed simultaneously or sequentially. In some embodiments the host cell is a plant cell and may be transformed via *Agrobacterium*-mediated transformation. The *Agrobacterium* transformation vector may comprise one or more T-DNA sequences adjacent to one or more border sequences. In another embodiment, a (trans)gene of interest is positioned within a T-DNA region, adjacent to or flanked by one or more border sequences for transfer into the host cell. Thus, transfer of the gene of interest may be facilitated due to the suppression of expression of a XRCC4, KU70, KU80, ATM or DNA-PKc gene in a host cell.

In yet another aspect, the invention provides a plant genetic regulatory element comprising the XRCC4 promoter (SEQ ID NO:9), or a fragment thereof with promoter activity. Gene regulatory sequences upstream and downstream of the XRCC4 coding region, and fragments thereof with promoter activity, such that of SEQ ID NO:9 are contemplated. In one embodiment, the present invention provides a promoter comprising a polynucleotide sequence substantially similar to the polynucleotide sequence of SEQ ID NO:9, or any fragments or variants thereof that are capable of regulating transcription of operably linked polynucleotide molecules, e.g., having promoter activity. In particular embodiments, a fragment of a promoter sequence provided herein is defined as comprising at least about 50, 75, 100, 125, 150, 200, 250, 300, 350, 400, 450, 500, 600, 750, 900, 1000, or more contiguous nucleotides of the promoter sequence, such as SEQ ID NO:9, up to the full length of the sequence.

Of particular interest are polynucleotide molecules wherein the polynucleotide molecules function in plants to direct transcription (i.e. display promoter activity) and have at least about 60% sequence identity, at least about 70% sequence identity, at least about 80% sequence identity, at least about 90% sequence identity, or even greater sequence identity, specifically including about 73%, 75%, 78%, 83%, 85%, 88%, 92%, 93%, 94%, 95%, 96%, 97%, 98%, or 99% or greater sequence identity with the nucleotide sequence of SEQ ID NO:9. In certain embodiments of the invention, nucleic acids hybridizing to SEQ ID NO:6, or SEQ ID NO:9 or a complement or reverse complement thereof, under stringent conditions are provided. Such conditions are well known in the art, such as 5×SSC, 50% formamide and 42° C., or 1X (or less) SSC and 65° C. The invention further provides nucleic acid sequences that encode a sequence complementary to all or a part of an mRNA encoded by a gene in DNA-repair pathway, as described herein and known in the art, wherein the expression of the sequences functions to down-regulate the gene. In specific embodiments the gene may be down-regulated wherein the efficiency by which the cell is transformed is increased relative to an otherwise isogenic cell in which the gene is not down-regulated. In further specific embodiments, transformation efficiency may be increased by 25%, 50%, 75%, 100% and greater that 100% relative to an otherwise isogenic control cell.

There are conflicting reports about the role of the non-homologous end-joining (NHEJ) protein KU80 in T-DNA integration. Gallego et al. (2003) found no deficiency in T-DNA integration in KU80 mutants, while Friesner and Britt (2003) showed a reduction in T-DNA integration in KU80 mutants. Subsequently Li et al. (2005) showed that KU80 mutants showed decreased T-DNA integration while overexpressors of KU80 showed increased susceptibility to *Agrobacterium* infection and increased resistance to DNA-damaging agents. The characterization of VirE2-interacting proteins VIP1, by Tzfira et al., (2002); Li et al. (2005), and VIP2 by Anand et al. (2007) also point to the role of these genes in T-DNA integration. Studies in a yeast T-DNA integration system have identified yeast genes required for integration both via non-homologous recombination and homologous recombination (van Attikum and Hooykaas, 2003, van Attikum et al., 2001).

The principal components of the NHEJ pathway are the KU70-KU80 heterodimer, the DNA-activated Protein Kinase (DNA-Pkcs), the ATM and the ATR kinases, and the XRCC4-Lig IV complex (FIG. 1; Weterings and Chen, 2007). Accessory factors like Polymerase µ, TdT, Artemis, Polymerase lambda and others are also involved. The closing of the double strand break (DSB), mediated by the XRCC4-Ligase IV complex and affecting the insertion of any foreign molecule into the genome like T-DNA is apparently an important step in the DNA-repair process. Thus, although certain examples focus on the role of XRCC4 in affecting the process of T-DNA integration, other members of the NHEJ pathway for whom corresponding *Arabidopsis* genes have been identified in the database, and homozygous exon knockouts have been obtained, have also been evaluated using the described assays, and suppression of expression of other DNA-repair pathway genes has also resulted in increased transformation, further demonstrating the utility of this overall approach. In particular, observations concerning the effect on transformation efficiency of *Arabidopsis* knockouts for the genes KU70, KU80, and ATM, show increased transformation efficiency. Also, similarly to XRCC4, homozygous exon knockouts in *Arabidopsis* of the gene DNA-PKc could not be identified, suggesting that a homozygous knockout is lethal. A heterozygous exon knockout though is viable. Further experiments are being pursued to confirm these above observations The disclosed VIGS experiments in *N. benthamiana* mimic the RNAi events in *Arabidopsis*, and both of these approaches illustrate an increase in transformation efficiency when XRCC4 is silenced in these two different model systems. The opposite effect is observed upon over-expression of this gene in *Arabidopsis*, i.e. a drastic decrease in transformation efficiency. These two approaches (i.e. over-expression or suppression of XRCC4 expression), and the described results, demonstrate that XRCC4 acts in allowing access of foreign DNA (e.g. T-DNA) to double strand breaks in a recipient or host cell genome, and that controlling the expression of this gene is a useful strategy for increasing genetic transformation. Further, increasing transformation efficiency by reducing the expression of a XRCC4 gene in a DNA-recipient cell is not limited to *Agrobacterium*-mediated genetic transformation. An additional aspect of the invention is a method for increasing transformation efficiency by using a DNA damaging agent like Bleomycin which induces DSBs in DNA. Incorporating the use of such a DSB-inducing agent during transformation, for instance when expression of a gene encoding an NHEJ pathway component is being suppressed, could also increase transformation efficiency.

Over-expression of a DSB (NHEJ) DNA repair gene such as XRCC4 results in a loss of efficiency of *Agrobacterium*-mediated genetic transformation, which is necessary for Crown Gall to occur. Thus methods and compositions relating to such over-expression are other aspects of the invention and also allow for reducing the occurrence of Crown Gall, e.g. plant infection or symptoms, in crop plants such as grapes and roses, and other ornamental plants, among others.

I. Plant Expression Constructs and Nucleic Acids

In one aspect of the invention, a plant transformation vector comprising a nucleic acid of a gene in the NHEJ pathway, including sequences that encode an mRNA complementary to all or a portion thereof, such as the KU70-KU80 heterodimer, the DNA-activated Protein Kinase (DNA-Pkcs), the ATM and the ATR kinases, and the XRCC4-Lig IV complex are provided. An exemplary construct may comprise a promoter functional in a plant operably linked to a nucleic acid sequence encoding a XRCC4 polypeptide, or fragment thereof. Examples of regulatory sequences which may be used to drive expression of a such a sequence in a host cell include the CaMV 35S promoter, nopaline synthase promoter, or TRV promoter, functional in plant cells. The promoter may be a constitutive promoter or an inducible promoter.

In one embodiment of the invention, a nucleic acid sequence is therefore provided that comprises a sequence encoding a polypeptide as set forth in the Sequence Listing, as well as fragments and complements thereof thereof, including those sequence encoding a polypeptide which exhibit enzyme activity and have at least 80%, 85%, more preferably at least 90% identity, at least about 95% identity, or at least about 98% or 99% identity to a polypeptide sequence, for instance an XRCC4 polypeptide, selected from the group of sequences set forth in the Sequence Listing. "Identity," as is well understood in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. Methods to determine "identity" are designed to give the largest match between the sequences tested. Moreover, methods to determine identity are codified in publicly available programs. "Identity" can be readily calculated by known methods including, but not limited to, those described in Computational Molecular Biology (1988); Biocomputing: Informatics and Genome Projects (1993); Computer Analysis of Sequence Data (1994); Sequence Analysis in Molecular Biology (1987); Sequence Analysis Primer (1991); and Carillo and Lipman (1988). Computer programs can be used to determine "identity" between two sequences these programs include but are not limited to, GCG (Devereux et al., 1984); suite of five BLAST programs, three designed for nucleotide sequences queries (BLASTN, BLASTX, and TBLASTX) and two designed for protein sequence queries (BLASTP and TBLASTN) (Coulson, 1994; Birren et al., 1997). The BLAST X program is publicly available from NCBI and other sources (BLAST Manual, Altschul et al., Altschul et al., 1990). The well known Smith Waterman algorithm can also be used to determine identity.

Parameters for polypeptide sequence comparison include the following: Algorithm: Needleman and Wunsch, (1970); Comparison matrix: BLOSSUM62 from Hentikoff and Hentikoff (1992); Gap Penalty: 12; and Gap Length Penalty: 4. A program which can be used with these parameters is publicly available as the "gap" program from Genetics Computer Group, Madison Wis. The above parameters along with no penalty for end gap may serve as default parameters for peptide comparisons.

Parameters for polynucleotide sequence comparison include the following: Algorithm: Needleman and Wunsch (1970); Comparison matrix: matches=+10; mismatches=0; Gap Penalty: 50; and Gap Length Penalty: 3. A program which can be used with these parameters is publicly available as the "gap" program from Genetics Computer Group, Madison Wis. The above parameters may serve as the default parameters for nucleic acid comparisons.

The invention therefore provides nucleic acids encoding polypeptide described herein. The nucleic acid may be defined as comprising nucleic acids encoding, in frame, the polypeptide. Those of skill in the art will understand in view of the disclosure that such nucleic acids may be provided as an expression construct by linking appropriate regulatory elements to the nucleic acid corresponding to a host cell in which heterologous expression is desired. For plant expression, a plant promoter may be operably linked to the nucleic acid. In addition, other elements such as enhancers, terminators and transit peptides may be used. Endogenous or heterologous elements may be used.

The construction of vectors which may be employed in conjunction with plant transformation techniques using these or other sequences according to the invention will be known to those of skill of the art in light of the present disclosure (see, for example, Sambrook et al., 1989; Gelvin et al., 1990). The techniques of the current invention are thus not limited to any particular nucleic acid sequences.

One important use of the sequences provided by the invention will be in the alteration of efficiency of genetic transformation by coding sequences that alter a plant phenotype as described herein, including for example a screenable or selectable marker gene phenotype or an agronomically important phenotype. The coding sequences may be provided with other sequences such as regulatory elements or other coding sequences. Where a selectable or screenable marker is used, one may employ the separate coding regions on either the same or different DNA segments for transformation. In the latter case, the different vectors are delivered concurrently to recipient cells to maximize co-transformation.

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce genes corresponding to an entire biosynthetic pathway into a plant. Introduction of such sequences may be facilitated by use of bacterial or yeast artificial chromosomes (BACs or YACs, respectively), or even plant artificial chromosomes. For example, the use of BACs for Agrobacterium-mediated transformation was disclosed by Hamilton et al. (1996).

Particularly useful for transformation are expression cassettes which have been isolated from such vectors. DNA segments used for transforming plant cells will, of course, generally comprise coding sequence which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. Preferred components that may be included with plant transformation vectors are as follows.

A. Regulatory Elements

Exemplary promoters for expression of a nucleic acid sequence in plants include the CaMV 35S promoter (Odell et al., 1985), CaMV 19S (Lawton et al., 1987), nos (Ebert et al., 1987), Adh (Walker et al., 1987), sucrose synthase (Yang and Russell, 1990), a-tubulin, actin (Wang et al., 1992), cab (Sullivan et al., 1989), PEPCase (Hudspeth and Grula, 1989) or R gene complex associated promoters (Chandler et al., 1989). Tissue specific promoters such as root cell promoters (Conkling et al., 1990) and tissue specific enhancers (Fromm et al., 1986) are also contemplated to be useful, as are inducible promoters such as ABA- and turgor-inducible promoters.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is envisioned that nucleic acids encoding a polypeptide as provided herein may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue.

B. Terminators

Transformation constructs prepared in accordance with the invention will typically include a 3' end DNA sequence that acts as a signal to terminate transcription and allow for the poly-adenylation of the mRNA produced by coding sequences operably linked to a promoter. Alternatively, a heterologous 3' end may enhance the expression of coding sequences. Examples of terminators that are deemed to be useful in this context include those from the nopaline synthase gene of Agrobacterium tumefaciens (nos 3' end) (Bevan et al., 1983), the terminator for the T7 transcript from the octopine synthase gene of Agrobacterium tumefaciens, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

D. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms selectable or screenable markers also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity.

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from Klebsiella ozaenae which confers resistance to bromoxynil (Stalker et al., 1988); a mutant acetolactate synthase (ALS) which confers resistance to imidazolinone, sulfonylurea or other ALS inhibiting chemicals (European Patent Application 154,204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; or a gene encoding for green fluorescent protein (Sheen et al., 1995; Haseloff et al., 1997; Reichel et al., 1996; Tian et al., 1997; WO 97/41228).

II. Antisense and RNAi Constructs

Antisense and RNAi treatments represent one way of altering transformation efficiency in accordance with the invention (e.g., by down regulation of a gene encoding a polypeptide involved in DSB DNA-repair). In particular, constructs comprising a coding sequence, including fragments thereof, in antisense orientation, or combinations of sense and antisense orientation, may be used to decrease or effectively eliminate the expression of a gene encoding a polypeptide involved in DSB DNA-repair in a host cell such as a plant, to obtain an improvement in transformation efficiency as is described herein. Accordingly, this may be used to suppress the expression and function of a DNA-repair coding sequence or homologous sequence thereof. In particular embodiments, expression of a gene encoding XRCC4 or other gene encoding a component of a eukaryotic cell DNA repair pathway, such as the NHEJ pathway, is suppressed.

Techniques for RNAi are well known in the art and are described in, for example, Lehner et al., (2004) and Downward (2004). The technique is based on the fact that double stranded RNA is capable of directing the degradation of messenger RNA with sequence complementary to one or the other strand (Fire et al., 1998). Therefore, by expression of a particular coding sequence in sense and antisense orientation, either as a fragment or longer portion of the corresponding coding sequence, the expression of that coding sequence can be down-regulated.

Antisense, and in some aspects RNAi, methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense oligonucleotides, when introduced into a target cell, specifically bind to their target polynucleotide and interfere with transcription, RNA processing, transport, translation and/or stability. Antisense and RNAi constructs, or DNA encoding such RNA's, may be employed to inhibit gene transcription or translation or both within a host cell, either in vitro or in vivo, such as within a host plant cell. In certain embodiments of the invention, such an oligonucleotide may comprise any unique portion of a nucleic acid sequence provided herein. In certain embodiments of the invention, such a sequence comprises at least 18, 30, 50, 75 or 100 or more contiguous nucleic acids of the nucleic acid sequence of a gene encoding a component of a DNA repair pathway, such as the NHEJ pathway, and/or complements thereof, which may be in sense and/or antisense orientation. By including sequences in both sense and antisense orientation, increased suppression of the corresponding coding sequence may be achieved.

Constructs may be designed that are complementary to all or part of the promoter and other control regions, exons, introns or even exon-intron boundaries of a gene. It is contemplated that the most effective constructs may include regions complementary to intron/exon splice junctions. Thus, it is proposed that a preferred embodiment includes a construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an RNAi or antisense construct which has limited regions of high homology, but also contains a non-homologous region (e.g., ribozyme; see above) could be designed. Methods for selection and design of sequences that generate RNAi are well known in the art (e.g., Reynolds, 2004). These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence. Constructs useful for generating RNAi may also comprise concatemers of sub-sequences that display gene regulating activity. Other methods for gene suppression may also be utilized, for instance virus induced gene silencing (VIGS; e.g. Burch-Smith et al., 2004) and as described herein.

III. Methods for Genetic Transformation

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by *Agrobacterium*-mediated transformation (U.S. Pat. No. 5,591,616 and U.S. Pat. No. 5,563,055; both specifically incorporated herein by reference) and by acceleration of DNA coated particles (U.S. Pat. No. 5,550,318; U.S. Pat. No. 5,538,877; and U.S. Pat. No. 5,538,880; each specifically incorporated herein by reference in its entirety), etc. Through the application of techniques such as these, the cells of virtually any plant species may be stably transformed, and these cells developed into transgenic plants.

A. *Agrobacterium*-Mediated Transformation

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation is most efficient in dicotyledonous plants and is the preferable method for transformation of dicots, including *Arabidopsis*, tobacco, tomato, alfalfa and potato. Indeed, while *Agrobacterium*-mediated transformation has been routinely used with dicotyledonous plants for a number of years, it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998) and maize (Ishidia et al., 1996).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

B. Electroporation

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

C. Microprojectile Bombardment

Another method for delivering transforming DNA segments to plant cells in accordance with the invention is microprojectile bombardment (U.S. Pat. No. 5,550,318; U.S. Pat. No. 5,538,880; U.S. Pat. No. 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al. 1994), peanut (Singsit et al., 1997), cotton (McCabe and Martinell, 1993), tomato (VanEck et al. 1995), and legumes in general (U.S. Pat. No. 5,563,055, specifically incorporated herein by reference in its entirety).

D. Other Transformation Methods

Transformation of protoplasts can be achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts have been described (Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant lines that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cells are punctured. This technique has been used successfully with, for example, the monocot cereals maize (PCT Application WO 95/06128, specifically incorporated herein by reference in its entirety (Thompson, 1995), and rice (Nagatani, 1997).

E. Tissue Cultures

Tissue cultures may be used in certain transformation techniques for the preparation of cells for transformation and for the regeneration of plants therefrom. Maintenance of tissue cultures requires use of media and controlled environments.

"Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. Bactoagar (e.g. Difco Laboratories, Detroit, Mich.), Hazelton agar, Gelrite, and Gelgro are specific types of solid support that are suitable for growth of plant cells in tissue culture.

Some cell types will grow and divide either in liquid suspension or on solid media. As disclosed herein, plant cells will grow in suspension or on solid medium, but regeneration of plants from suspension cultures typically requires transfer from liquid to solid media at some point in development. The type and extent of differentiation of cells in culture will be affected not only by the type of media used and by the environment, for example, pH, but also by whether media is solid or liquid.

Tissue that can be grown in a culture includes meristem cells, Type I, Type II, and Type III callus, immature embryos and gametic cells such as microspores, pollen, sperm and egg cells. Type I, Type II, and Type III callus may be initiated from tissue sources including, but not limited to, immature embryos, seedling apical meristems, root, leaf, microspores and the like. Those cells which are capable of proliferating as callus also are recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population. For example, Type II callus development, followed by manual selection and culture of friable, embryogenic tissue, generally results in an enrichment of cells. Manual selection techniques which can be employed to select target cells may include, e.g., assessing cell morphology and differentiation, or may use various physical or biological means. Cryopreservation also is a possible method of selecting for recipient cells.

Manual selection of recipient cells, e.g., by selecting embryogenic cells from the surface of a Type II callus, is one means that may be used in an attempt to enrich for particular cells prior to culturing (whether cultured on solid media or in suspension).

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components, but may differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells previously have been described.

Examples of these media include, but are not limited to, the N6 medium described by Chu et al. (1975) and MS media (Murashige and Skoog, 1962).

IV. Production and Characterization of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

A. Selection

It is believed that DNA is introduced into only a small percentage of target cells in any one study. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphotransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*.

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on polypeptides encoded by the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/WO97/4103).

To use a bar-bialaphos or the EPSPS-glyphosate selective system, for example, transformed tissue can be cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate may be preferred, it is proposed that ranges of 0.1-50 mg/l bialaphos or 0.1-50 mM glyphosate will find utility.

B. Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins $m^{-2} s^{-1}$ of light. Plants may be matured in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants can be grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with $10^{-5}M$ abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of the exogenous gene through the use of techniques well known to those skilled in the art. Note, that intact sequences will not always be present, presumably due to rearrangement or deletion of sequences in the cell. The presence of DNA elements introduced through the methods of this invention may be determined, for example, by polymerase chain reaction (PCR™). Using this technique, discrete fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR™ analysis. In addition, it is not typically possible using PCR™ techniques to determine whether transformants have exogenous genes introduced into different sites in the genome, i.e., whether transformants are of independent origin. It is contemplated that using PCR™ techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR™, e.g., the presence of a gene.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations. These techniques are modifications of Northern blotting and will only demonstrate the presence or absence of an RNA species.

E. Gene Expression

While Southern blotting and PCR™ may be used to detect the gene(s) in question, they do not provide information as to whether the corresponding protein is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

V. Breeding Plants of the Invention

In addition to direct transformation of a particular plant genotype with a construct prepared according to the current invention, transgenic plants may be made by crossing a plant having a selected DNA of the invention to a second plant lacking the construct. For example, a selected polypeptide coding sequence can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

VI. Definitions

*Agrobacterium*-mediated transformation: Methods of *Agrobacterium*-mediated plant cell transformation include the use of bacterial strain(s) classified among the Rhizobiaceae, including *Agrobacterium* sp., *Rhizobium* sp., *Sinorhizobium* sp., among others. *Agrobacterium* may also mediate transformation of other eukaryotic cells, including fungal and insect cells.

Expression: The combination of intracellular processes, including transcription and translation undergone by a coding DNA molecule such as a structural gene to produce a polypeptide.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found In this respect, the sequence may be native to the host genome, but be rearranged with respect to other genetic sequences within the host sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an $R_0$ transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

$R_0$ transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce or has introduced into a plant genome by genetic transformation.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule designed for transformation into a host cell. Some vectors may be capable of replication in a host cell. A plasmid is an exemplary vector, as are expression cassettes isolated therefrom.

VII. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Identification of an XRCC4 Homolog in *N. benthamiana*

The ligase binding protein XRCC4, in *A. thaliana*, is a single copy gene (NM_113211 or At3G23100) on chromosome 3 (GenBank accession AF233528; West et al., 2000). The mRNA is 991 bases long (SEQ ID NO:1), encoding a 264 amino acid polypeptide (SEQ ID NO:2) which interacts with DNA ligase IV via a BRCT domain. The effect of alteration of expression of this gene was studied using Virus-induced gene silencing (VIGS) in the model plant *Nicotiana benthamiana* and by over-expression and RNAi studies in *Arabidopsis*.

Since a sequence homologous to *Arabidopsis* XRCC4 was not found in the EST databases of *N. benthamiana*, a tomato sequence (EST337143; see D'Agostino et al., 2006; SEQ ID NO:3) was used to design primers with attB1 and B2 sites (SEQ ID NOs:4-5) for Gateway® cloning (Life Sciences-Invitrogen Corp., Carlsbad, Calif.). Using these primers, a fragment of Nb-XRCC4 (SEQ ID NO:6) was PCR amplified from *N. benthamiana* cDNA and cloned into the TRV2 vector (Liu et al., 2002b), for VIGS. An alignment of *A. thaliana* and *N. benthamiana* XRCC4 sequences is shown in FIG. 2.

Example 2

Virus Induced Gene Silencing of XRCC4 in *N. benthamiana*

The TRV2::XRCC4 clone confirmed by DNA sequencing was introduced into *A. tumefaciens* strain GV2260, and was used to downregulate the endogenous *N. benthamiana* XRCC4 gene. Silenced *N. benthamiana* plants infected with TRV2::XRCC4 are phenotypically normal, like control TRV2::GFP plants. At about 18-21 days post silencing, leaves at the top of the silenced plants (12 plants per construct), which exhibited symptoms of viral spread (variegated symptoms) were harvested, surface sterilized and leaf discs (1 cm dia.) were cut from them. These leaf discs were infected with a tumorigenic strain of *Agrobacterium tumefaciens* strain A208, or with a disarmed strain of *Agrobacterium* carrying plasmid pCAS1 (e.g. Mysore et al., 2000; encoding a phosphinothricin resistance gene) at $OD_{600}$=0.2. After a period of 48 hrs for co-cultivation, leaf discs were either transferred onto MS-B media containing only antibiotics to kill the remaining *Agrobacterium* cells for the tumorigenesis assay, or onto callus inducing media containing phosphinothricin (5 mg/L) for the callus transformation assay. Leaf disc containing media were placed in growth chambers under light. After four weeks the fresh weight and dry weight of leaf discs were noted.

In all 4 experimental repeats were completed both at low and high OD (~0.4-0.45) of *Agrobacterium* inoculation of leaf discs, the XRCC4-silenced leaf discs showed a statistically significant increase in fresh weight and dry weight in both the tumor and callus transformation assays (FIG. 3). Also noteworthy was the increased number of leaf discs in the XRCC4 silenced plants that formed tumors or calli as compared to leaf discs from control plants. These experiments indicated that the down-regulation of XRCC4 expression leads to an increase in transformation efficiency.

Example 3

Studies on XRCC4 in *Arabidopsis thaliana*

In order to study the effect of loss of expression of the XRCC4 gene in *Arabidopsis*, available online T-DNA collections were mined for XRCC4 insertion mutants using BLAST tools. In spite of examining various resource collections, a true exon knockout of XRCC4 was not found in any collections, probably underlining the importance of this gene to the NHEJ machinery. One T-DNA insertion mutant found to have an insertion in an un-translated region of XRCC4 was found to still express the XRCC4 full-length transcript. This implies that a knockout of XRCC4 is most likely embryo-lethal in *Arabidopsis*. Therefore the role of this gene was studied using over-expression and down-regulation constructs.

1. Over-Expression Studies

Figure 4:
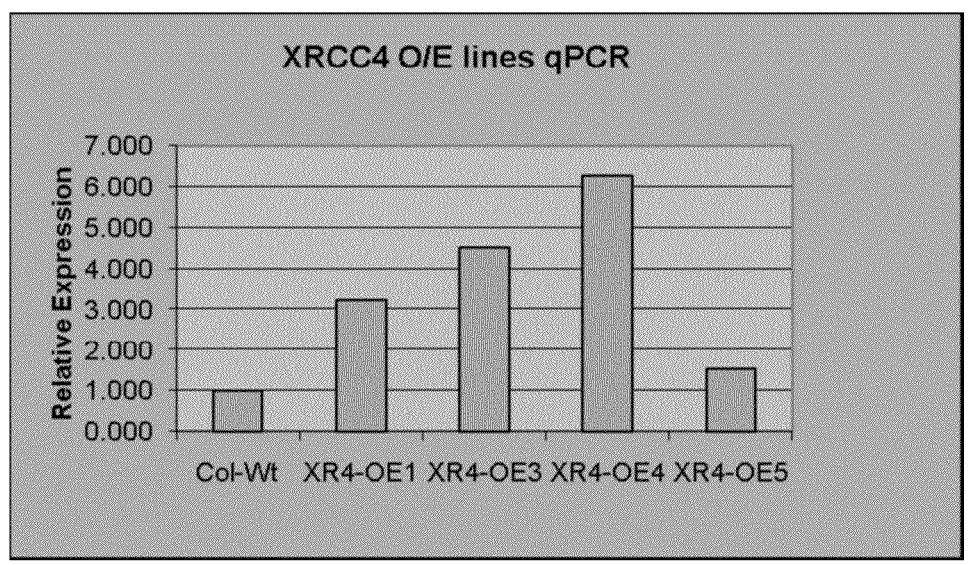
FIG. 4. Relative expression of XRCC4 in *A. thaliana* over-expression lines, determined by q-PCR.

Full-length XRCC4 sequence was cloned using attB1/B2 adapters XR4-AttB1-2 kb (ggggacaagtttgtacaaaaaagcaggctagtgggtcggtcccatttgtctat; SEQ ID NO:7), and XR4-AttB2-R (ggggaccactttgtacaagaaagctgggtccatctctaagttattgcatttac; SEQ ID NO:8), along with 2 Kb of its native promoter (SEQ ID NO:9), into the vector pMDC99 (Curtis & Grossniklaus, 2003) and the construct was introduced into *A. tumefaciens* GV3101 for transformation of *A. thaliana* using the floral dip method (Clough & Bent, 1998). T0 seeds from the transformed plants were screened on hygromycin containing media. Several independent events were screened by real-time quantitative PCR (qPCR) to confirm the upregulation of XRCC4 in these events. Three events showed significant up-regulation (FIG. 4) while one line showed only a slight change in expression. Progeny from the T2 generation of these events were subjected to tumorigenesis and callus transformation assays (as described for leaf discs, in Example 2 above), using root explants.

Roots of axenically grown plants were chopped up using a scalpel blade into 0.5 cm segments and then co-cultivated with low OD cultures ($OD_{600}$=0.01-0.02) of either a tumor-inducing strain or a disarmed strain of *Agrobacterium* carrying plasmid pCAS1 (encodes a phosphinothricin resistance gene). After 48 hrs of co-cultivation, the roots exposed to the tumor-inducing strain were moved to MS-B containing media with antibiotics to kill the *Agrobacterium*, while the roots exposed to pCAS1 harboring strain were moved to a callus inducing medium containing phosphinothricin (10 mg/L) and antibiotics to kill *Agrobacterium*. After 4 weeks results were noted. All over-expression events exhibited either a complete lack of transformed root segments or a 1-2% level of transformation as compared to Col-0 wild-type controls in both the tumorigenesis and callus transformation assays (FIG. 5), indicating that XRCC4 over-expression lead to increased efficiency of DSB closure, leading to a lack of open DSBs for T-DNA insertion and hence decreased transformation.

2. Result of Suppression of XRCC4 via RNAi

A 246 bp XRCC4 gene fragment encompassing 85 bp of the exon prior to the TAA stop codon and the rest of the 3'-UTR was cloned using attB1/B2 primers XR4i-B1-F (forward primer for RNAi construct; ggggacaagtttgtacaaaaaagcaggct gaagtgatgatgagaagagcgagga; SEQ ID NO:10) and XR4-AttB2-R (reverse primer for RNAi construct; ggggaccactttgtacaagaaagctgggtccatctctaagttattgcatttac; SEQ ID NO:11) into the RNAi vector pK7GWIWG2(I) (Karimi et al., 2002), and the construct was introduced into *A. tumefaciens*

Figure 6:
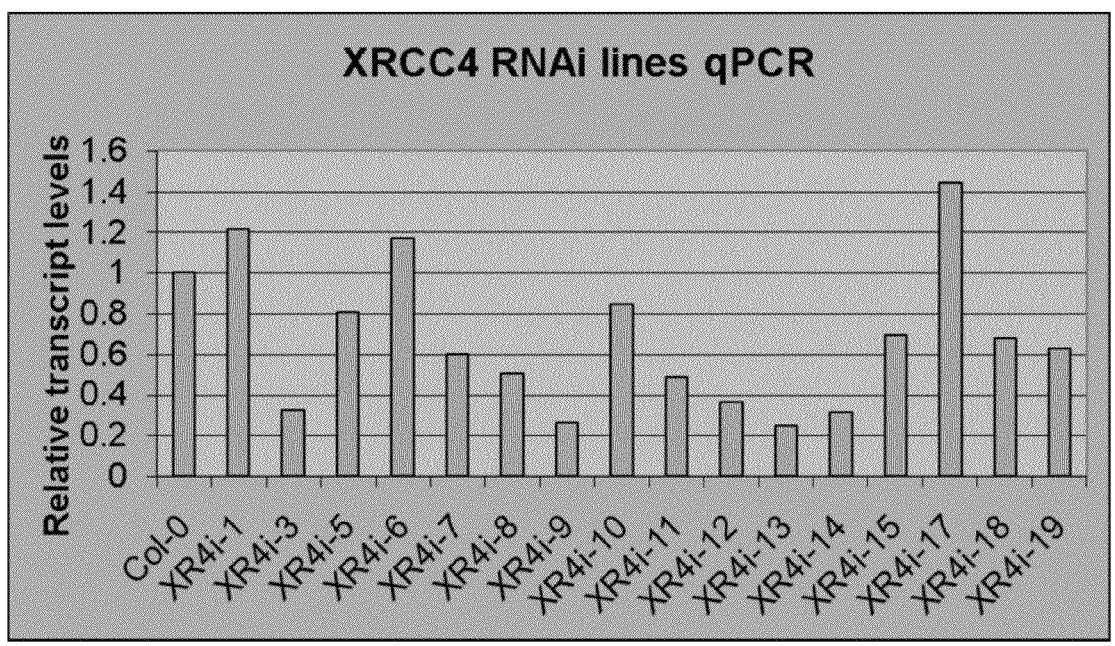
FIG. 6. Relative expression of XRCC4 in *A. thaliana* lines undergoing RNAi-mediated suppression of expression of XRCC4.

GV3101 using electroporation. Floral dip transformation of *A. thaliana* resulted in T0 seeds which were screened on kanamycin containing media. More than 20 independent events were collected and the down-regulation status of XRCC4 gene was examined in these events by qPCR (FIG. 6) using primers XR4 RT-F (SEQ ID NO:12: ggcacttggcataattctcgtt), and XR4 RT-R (SEQ ID NO:13: tcgcattgcaaatccaagagga), which showed that most of the events were indeed down-regulated from 20-70% in XRCC4 expression. Based on a preliminary screen of all events using the root tumor assay, three events, labeled XR4i-3, 25 and 31, were examined further by root tumor assay using multiple replicates, as described above.

Figure 7:
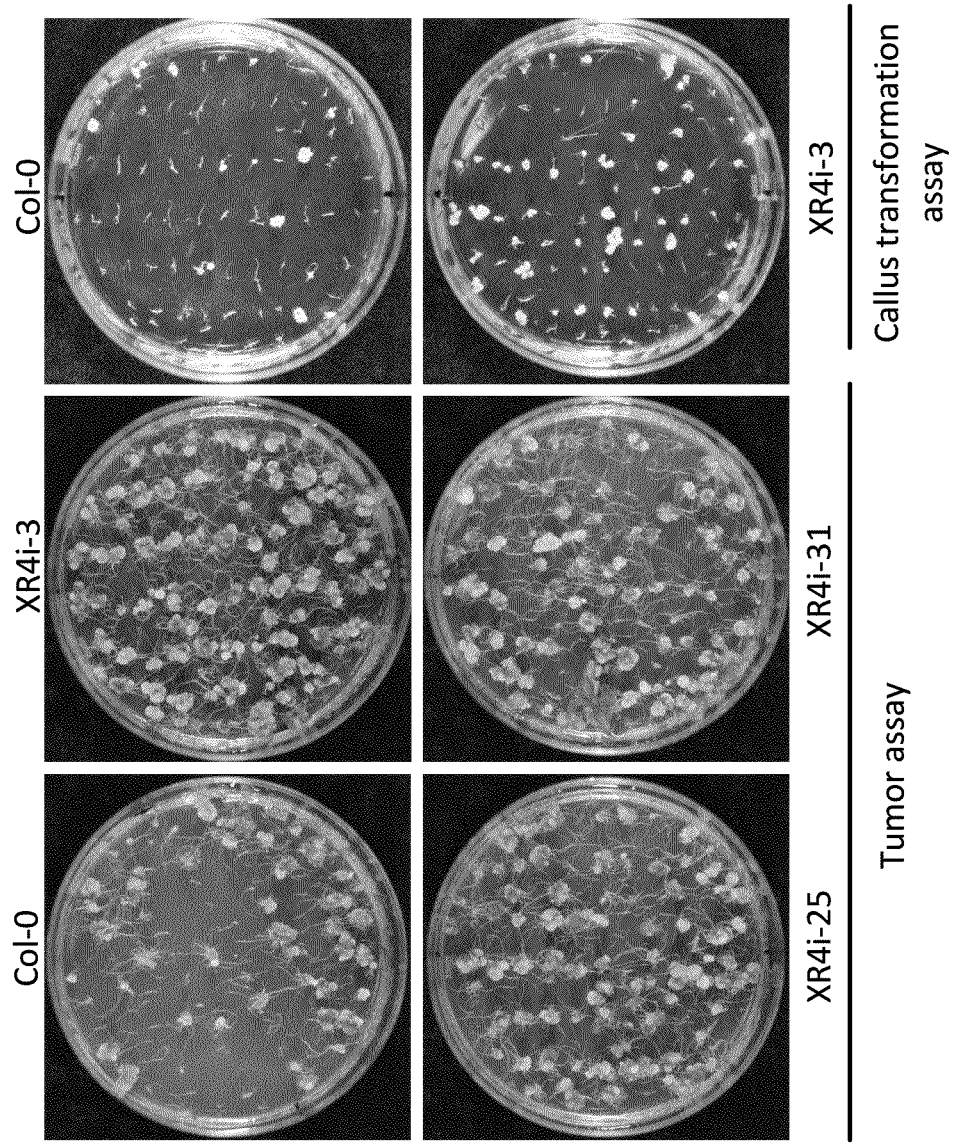
FIG. 7. Exemplary XRCC4 RNAi lines showing increased transformation.

Roots of axenically grown plants were chopped up using a scalpel blade into 0.5 cm segments and then co-cultivated with low OD cultures (OD600=0.01-0.02) of either a tumor-inducing strain or a disarmed strain of *Agrobacterium* carrying plasmid pCAS1 (encodes a phosphinothricin resistance gene). After 48 hrs of co-cultivation, the roots exposed to the tumor-inducing strain were moved to MS-B containing media with antibiotics to kill the *Agrobacterium*, while the roots exposed to the pCAS1 harboring strain were moved to a callus inducing medium containing phosphinothricin (10 mg/L) and antibiotics to kill *Agrobacterium*. After 4 weeks results were noted. All three events showed increases in transformation (50% in wild-type to 80-100% in the RNAi lines) (FIG. 7). These results indicate that the down-regulation of XRCC4 leads to a decreased efficiency of DSB closure and hence more DSBs are available for T-DNA integration, thus leading to increase in transformation.

Example 4

Effect of Suppression of Other DNA Repair-Pathway Genes on Transformation Efficiency Other genes encoding polypeptides involved in DSB DNA-repair, such as members of the NHEJ DNA-repair pathway are also attractive targets for manipulation to improve transformation efficiency. Some corresponding *Arabidopsis* genes have been identified in the database and, for some, homozygous exon knockouts have been obtained. These were evaluated using the described assays. Suppression of the KU70, KU80 and ATM genes (see FIG. 1, and Weterings & Chen, 2007) has also resulted in increased transformation efficiency, further demonstrating the utility of this overall approach. Also, similar to XRCC4, homozygous exon knockouts of the gene DNA-PKc could not be identified, suggesting that a homozygous knockout is lethal. A heterozygous exon knockout line is however viable, and this gene thus represents another target for manipulation to increase genetic transformation efficiency.

Example 5

Increasing Transformation Efficiency by Treatment of Cells with a DNA Damaging Agent The preceding examples have shown the importance of modulation of the level of DNA-repair in affecting transformation efficiency. Accordingly, an increase in transformation efficiency may be obtained by treating explants with a DNA damaging agent such as Bleomycin, which induces DSBs in a cell's genome. Such treatment may be performed in conjunction with suppression of expression of a gene encoding a polypeptide that functions in DNA repair, for instance before or during transformation of a plant cell (e.g. a co-culture step) using a member of the Rhizobacteriaceae. Alternatively, such treatment of a DNA-recipient cell could be performed during a transformation process achieved by another method, such a electroporation or microprojectile bombardment.

Example 6

Effect of Suppression of Expression of XRCC4 on Susceptibility of Host Plant Cells to Crown Gall Disease Crown Gall disease, caused by *A. tumefaciens* and related Agrobacteria, may be a significant disease on certain crop plants (e.g. Anand and Mysore, 2006). Since, as shown in preceding examples, over-expression of DSB (NHEJ) DNA repair genes such as XRCC4 resulted in a loss of efficiency of *Agrobacterium*-mediated genetic transformation, which is necessary for Crown Gall to occur, such over-expression represents a viable strategy for reducing plant infection or symptoms, and controlling crown gall disease in crop plants, such as grapes and roses, among others.

Example 7

Interaction of XRCC4 with VirE2 in a Yeast 2-Hybrid Assay

Figure 8:
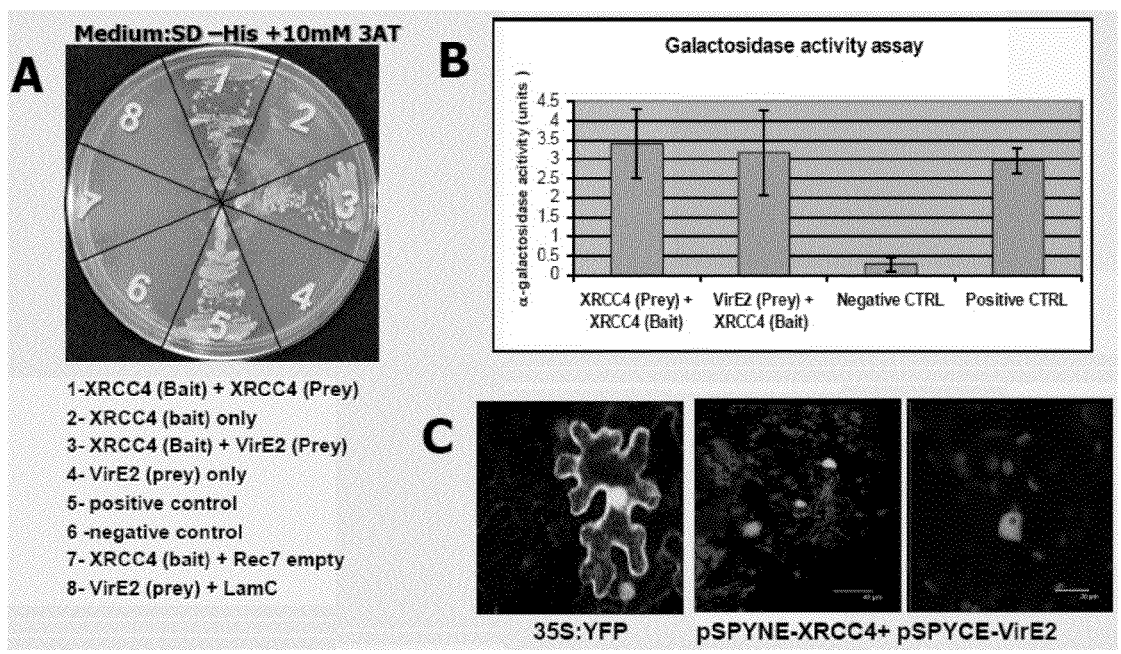
FIG. 8. Interaction between XRCC4 and VirE2 as shown in 2-hybrid assay. (A) Y2H interactions demonstrating XRCC4 dimerization and interaction with VirE2; (B) β-galactosidase activity assay confirms interaction of VirE2 and XRCC4; (C) in planta BiFC assay confirms XRCC4:VirE2 interaction in plant.

A yeast 2-hybrid assay for interaction between XRCC4 and *Agrobacterium* proteins showed interaction with VirE2 (FIG. 8). The interaction of these two proteins was shown in yeast using two-hybrid specific vectors and strains and further confirmed by a beta-galactosidase assay to quantitate the interaction as shown in the figure. The in planta interaction of these two proteins in the nuclear compartment was shown by Bimolecular Fluorescence Complementation ("BiFC"), using constructs pSPYNE:XRCC4 and pSPYCE:VirE2 (see Walter et al., (2004)), which harbor a split YFP (yellow fluorescent protein; GFP variant) construct. BiFC is based on the association between fragments of a fluorescent protein when they are tethered in the same macromolecular complex. The split constructs were introduced separately into *A. tumefaciens* GV2260 by electroporation and then co-infiltrated into *N. benthamiana* leaves at equal $OD_{600}$ of 0.8-1.0. Leaves were also infiltrated with a full-length 35S:YFP construct separately as controls. After 48 hrs infiltrated leaves were observed for fluorescence under a confocal microscope.

Example 8

Increased T-DNA Integration in XRCC4 Silenced Tissues Under No-Selection Pressure A reporter construct pBISN1 harboring a GUS reporter gene containing intron (Narasimhulu et al. 1996) was used in a T-DNA integration assay wherein a no-selection pressure strategy is used during the assay. Leaf discs from *N. benthamiana* plants silenced for NbXRCC4 using the VIGS protocol (as outlined in Example 2) were challenged with a non-tumorigenic strain of *A. tumefaciens* GV2260 harboring pBISN1 and plated for callus formation on callus induction medium with no selection pressure. Calli formed after three weeks were individually cultured in a liquid callus induction medium (containing antibiotics to kill *Agrobacterium*) with gentle shaking and continuous light for formation of suspension cell cultures. These suspension cultures were sub-cultured every two weeks for 5-6 times. After final subculture, cells were harvested by filtration and genomic DNA extracted using Plant DNAzol solution (Invitrogen). Equal amounts of undigested control (TRV:GFP-silenced tissues) and XRCC4 (TRV:XRCC4-silenced tissues) DNA was run onto a gel and gel blot analysis carried out using a DIG-labelled uidA gene probe (Mysore et al., 2000). Gel blot analysis conclusively showed that XRCC4-silenced leaf discs samples showed a higher signal intensity over controls indicating the integration of more T-DNA copies within these tissues over control.

Example 9

Increase in T-DNA Integration Seen in a Promoter-Less GUS Assay

Figure 9:
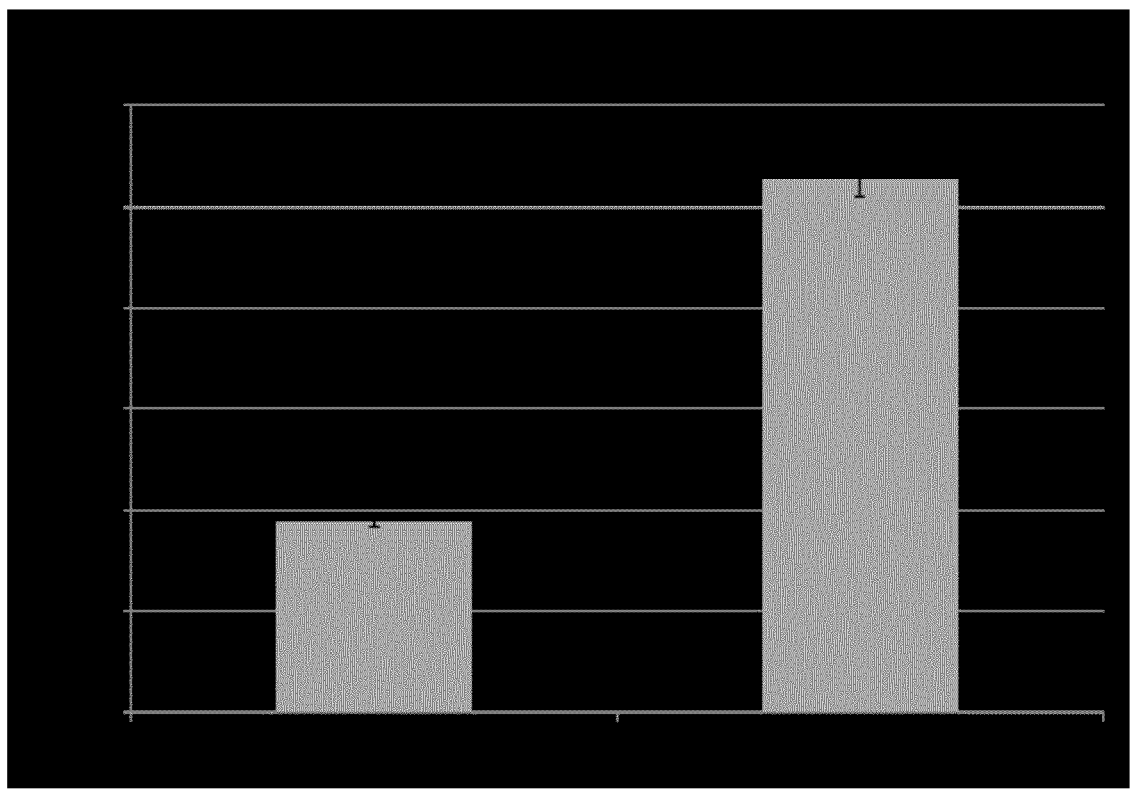
FIG. 9. Graph shows GUS expression from a promoter-less construct (pKM1) in leaf tissue from control and XRCC4-silenced leaf discs of *Nicotiana benthamiana*.

To further deomonstrate that XRCC4 downregulation causes increased T-DNA integration, control and XRCC4-silenced leaf discs (from Example 2) of *Nicotiana benthamiana* were challenged with a promoter-less GUS construct pKM1 (Mysore et al. 1998) harbored within *A. tumefaciens* GV2260. Leaf discs were placed on callus induction without selection pressure for callus formation for three weeks following which individual calli were ground up for protein extraction and a GUS flourescence assay was carried out (Jefferson et al. 1987). The results (FIG. 9) clearly show an increase in GUS expression in XRCC4 silenced tissues over control tissues, suggesting increased integration of T-DNA near promoter-rich regions allowing GUS expression.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. No. 4,535,060; U.S. Pat. No. 5,302,523; U.S. Pat. No. 5,322,783; U.S. Pat. No. 5,384,253; U.S. Pat. No. 5,464,765; U.S. Pat. No. 5,508,184; U.S. Pat. No. 5,538,877; U.S. Pat. No. 5,538,880; U.S. Pat. No. 5,545,818; U.S. Pat. No. 5,550,318; U.S. Pat. No. 5,563,055; U.S. Pat. No. 5,563,055; U.S. Pat. No. 5,591,616; U.S. Pat. No. 5,610,042; U.S. Pat. No. 5,91,616
U.S. Publn. 20030233676
Abdullah et al., *Biotechnology*, 4:1087, 1986.
Altschul et al., *J. Mol. Biol.*, 215:403-410, 1990.
Anand and Mysore, In: *Advances Plant Physiol.*, Scientific Publishers, Jodhpur, 2005.
Anand and Mysore, *Agrobacterium Biology and Crown Gall Disease*, pp. 359-384 in S. S. Gnanamanickam, ed., *Plant Associated Bacteria*, Springer, 2006.
Anand et al., *Plant Cell* 19:1695-1708, 2007.
Bates, *Mol. Biotechnol.*, 2(2):135-145, 1994.
Battraw and Hall, *Theor. App. Genet.*, 82(2):161-168, 1991.
Bevan et al., *Nucleic Acids Res.*, 11(2):369-385, 1983.
Bhattacharjee et al., *J. Plant Bioch. Biotech.*, 6(2):69-73. 1997.
Biocomputing: Informatics and Genome Projects, Smith (Ed.), Academic Press, NY, 1993.
Birren, et al., *Genome Analysis*, 1:543-559, 1997.
Bower et al., *Plant J.*, 2:409-416. 1992.
Bradford, *Anal. Biochem.* 72:248-254, 1976.
Broothaerts et al., *Nature* 433:629-633, 2005.
Buising and Benbow, *Mol. Gen. Genet.*, 243(1):71-81, 1994.
Bundock, et. al., *EMBO J.* 14:3206-3214, 1995.
Burch-Smith et al., *Plant J.*, 39:734-746, 2004.
Callis et al., *Genes Dev.*, 1:1183-1200, 1987.
Carillo and Lipman, *J. Applied Math.*, 48:1073, 1988.
Casas et al., *Proc. Natl. Acad. Sci. USA*, 90:11212-11216, 1993.
Chandler et al., *Plant Cell*, 1:1175-1183, 1989.
Christou et al., *Proc. Natl. Acad. Sci. USA*, 84:3962-3966, 1987.
Chu et al., *Scientia Sinica*, 18:659-668, 1975.
Clough & Bent, *Plant J.* 16:735-743, 1998.
Computational Molecular Biology, Lesk (Ed.), Oxford University Press, NY, 1988.
Computer Analysis Sequence Data, Part I, Griffin and Griffin (Eds.), Humana Press, NY, 1994.
Conkling et al., *Plant Physiol.*, 93:1203-1211, 1990.
Coulson, *Trends in Biotech.*, 12:76-80, 1994.
Curtis & Grossniklaus, *Pl. Physiol.* 133:462-469, 2003.
D'Agostino et al., *NAR* 35:D901-D905, 2006.
D'Halluin et al., *Plant Cell*, 4:1495-1505, 1992.
DE 3642 829 A
Dellaporta et al., In: *Chromosome Structure and Function: Impact of New Concepts*, 18th Stadler Genetics Symposium, 11:263-282, 1988.
Downward, *BMJ*, 328(7450):1245-1248, 2004.
Ebert et al., *Proc. Natl. Acad. Sci. USA*, 84:5745-5749, 1987.
EP 154,204
Fire et al., *Nature*, 391: 806-11, 1998.
Forsthoefel et al., *Aust J Plant Physiol.*, 19:353-366, 1992.
Fraley et al., *Bio/Technology*, 3:629-635, 1985.
Friesner and Britt, *Plant J.* 34:427-440, 2003.
Fromm et al., *Nature*, 319(6056):791-793, 1986.
Gallego et al., *Plant Cell* 15:782-789, 2003.
Gallie et al., *Plant Cell*, 1:301-311, 1989.
Gelvin et al., In: *Plant Molecular Biology Manual*, Kluwer Academic Publishers, 1990.
Gelvin, *Microbiol. Molec. Biol. Rev.*, 67:16-37, 2003.
Ghosh-Biswas et al., *J. Biotechnol.*, 32(1):1-10, 1994.
Hagio et al., *Plant Cell Rep.*, 10(5):260-264, 1991.
Hamilton et al., *Proc. Natl. Acad. Sci. USA*, 93:9975-9979, 1996.
Haseloff et al., *Proc. Natl. Acad. Sci. USA*, 94(6):2122-2127, 1997.
He et al., *Plant Cell Reports*, 14 (2-3):192-196, 1994.
Hensgens et al., *Plant Mol. Biol.*, 22(6):1101-1127, 1993.
Hentikoff and Hentikoff, *Proc. Natl. Acad. Sci USA*, 89:10915-10919, 1992.
Hiei et al., *Plant. Mol. Biol.*, 35(1-2):205-218, 1997.
Hinchee et al., *Bio/Technology*, 6:915-922, 1988.
Hou and Lin, *Plant Physiology*, 111:166, 1996.
Hudspeth and Grula, *Plant Mol. Biol.*, 12:579-589, 1989.
Ikuta et al., *BioTechnol.*, 8:241-242, 1990.
Ishida et al., *Nat. Biotechnol.*, 14(6):745-750, 1996.
Jefferson et al., *EMBO J.*, 6:901-907, 1987.
Kaeppler et al., *Plant Cell Rep.*, 8:415-418, 1990.
Kaeppler et al., *Theor. Appl. Genet.*, 84(5-6):560-566, 1992.
Karimi, et al., *Trends Plant Sci.* 7:193-195, 2002.

Katz et al., *J. Gen. Microbiol.*, 129:2703-2714, 1983.
Klee et al., *Bio-Technology*, 3(7):637-642, 1985.
Knittel et al., *Plant Cell Reports*, 14(2-3):81-86, 1994.
Lawton et al., *Plant Mol. Biol.* 9:315-324, 1987.
Lazzeri, *Methods Mol. Biol.*, 49:95-106, 1995.
Lee et al., *Korean J. Genet.*, 11(2):65-72, 1989.
Lehner et al., *Brief Funct Genomic Proteomic, April;* 3(1): 68-83, 2004.
Li et al., *Proc. Natl. Acad. Sci. USA*, 102:19231-19236, 2005.
Liu et al., *EMBO J.*, 17:1096-1106, 1998.
Liu et al., *Plant J.*, 30:415-429, 2002.
Lorz et al., *Mol Gen Genet*, 199:178-182, 1985.
Marcotte and Bayley, *Nature*, 335(6189):454-457, 1988.
McCabe and Martinell, *Bio-Technology*, 11(5):596-598, 1993.
McCormac et al., *Euphytica*, 99(1):17-25, 1998.
Murashige and Skoog, *Physiol. Plant*, 15:473-497, 1962.
Mysore et al, *MPMI*, 11:668-683, 1998.
Mysore et al., *Plant J.* 21:9-16, 2000.
Nagatani et al., *Biotech. Tech.*, 11:471-473, 1997.
Nam et al., *Mol. Gen. Genet.*, 261:429-438, 1999.
Narasimhulu et al, *Plant Cell*, 8:873-886, 1996.
Needleman and Wunsch, *J. Mol. Biol.*, 48:443-453, 1970.
Odell et al., *Nature*, 313:810-812, 1985.
Ogawa et al., *Sci. Rep.*, 13:42-48, 1973.
Omirulleh et al., *Plant Mol. Biol.*, 21:415-428, 1993.
Ow et al., *Science*, 234:856-859, 1986.
PCT Appln. WO 9217598
PCT Appln. WO 94/09699
PCT Appln. WO 95/06128
PCT Appln. WO 95/06128
PCT Appln. WO 97/41103
PCT Appln. WO 97/41228
Potrykus et al., *Mol. Gen. Genet.*, 199:169-177, 1985.
Reichel et al., *Proc. Natl. Acad. Sci. USA*, 93:5888-5893, 1996.
Reynolds, *Nat. Biotechnol.* 22:326-330, 2004.
Rhodes et al., *Methods Mol. Biol.*, 55:121-131, 1995.
Ritala et al., *Plant Mol. Biol.*, 24(2):317-325, 1994.
Rogers et al., *Methods Enzymol.*, 153:253-277, 1987.
Sambrook et al., In: *Molecular cloning: a laboratory manual*, 2$^{nd}$ Ed., Cold Spring Harbor Laboratory Press, Cold Spring Harbor, N.Y., 1989.
Sequence Analysis in Molecular Biology, von Heinje (Ed.), Academic Press, 1987.
Sequence Analysis Primer, Gribskov, and Devereux (Eds.), Stockton Press, NY, 1991.
Singsit et al., *Transgenic Res.*, 6(2):169-176, 1997.
Spencer et al., *Plant Mol. Biol.*, 18(2):201-210, 1992.
Stalker et al., *J. Biol. Chem.*, 263:6310-6314, 1988.
Sullivan et al., *Mol. Gen. Genet.*, 215(3):431-440, 1989.
Sutcliffe et al., *Proc. Natl. Acad. Sci. USA*, 75:3737-3741, 1978.
Thillet et al., *J. Biol. Chem.*, 263:12500-12508, 1988.
Thompson et al., *Nature Medicine*, 1:277-278, 1995.
Tian et al., *Genes Dev.*, 11(1):72-82, 1997.
Tian et al., *Plant Physiol.*, 135:25-38, 2004.
Tingay et al., *J. Plant*, 11(6):1369-1376. 1997.
Tomes et al., *Plant. Mol. Biol.*, 14(2):261-268, 1990.
Torbet et al., *Crop Science*, 38(1):226-231, 1998.
Torbet et al., *Plant Cell Reports*, 14:635-640, 1995.
Toriyama et al., *Theor Appl. Genet.*, 73:16, 1986.
Tsukada et al., *Plant Cell Physiol.*, 30(4)599-604, 1989.
Tzfira and Citovsky, *Curr. Opin. Biotechnol.*, 17:147-154, 2006.
Tzfira and Citovsky, *PNAS* 99:1043-1044, 2002.
Uchimiya et al., *Mol. Gen. Genet.*, 204(2):204-207, 1986.
Van Eck et al., *Plant Cell Reports*, 14(5):299-304, 1995.
Vasil et al., *Plant Physiol.*, 91:1575-1579, 1989.
Van Attikum & Hooykaas, *Nucl. Acids Res.*, 31, 826-832, 2003.
Van Attikum et al., *EMBO J.*, 20, 6550-6558, 2001.
Walker et al., *Proc. Natl. Acad. Sci. USA*, 84:6624, 1987.
Walter et al., *Plant J.*, 40:428-438, 2004.
Wang et al., *Am. J. Physiol.*, 263(4 Pt 1):G480-486, 1992.
West et al., *Plant J.* 24:67-78, 2000.
Weterings and Chen, *J. Cell Biol.* 179:183-186, 2007.
Yamada et al., *Plant Cell Rep.*, 4:85, 1986.
Yang and Russell, *Proc. Natl. Acad. Sci. USA*, 87:4144-4148, 1990.
Zheng and Edwards, *J. Gen. Virol.*, 71:1865-1868, 1990.
Zhou et al., *Exp. Hematol*, 21:928-933, 1993.
Zukowsky et al., *Proc. Natl. Acad. Sci. USA*, 80:1101-1105, 1983.

---

What is claimed is:

1. A transgenic plant or a part thereof comprising a polynucleotide sequence that encodes a sequence complementary to all or part of an XRCC4 mRNA, wherein said polynucleotide sequence suppresses expression of XRCC4 in the plant, wherein the polynucleotide sequence is linked to a heterologous promoter functional in the plant or part thereof, wherein the plant or part thereof exhibits increased transformation efficiency relative to an otherwise isogenic plant or part thereof lacking the polynucleotide sequence.

2. The plant of claim 1, wherein the plant is a monocotyledonous plant or a dicotyledonous plant.

3. A cell of the plant of claim 1.

4. A seed of the plant of claim 1, wherein the seed comprises the polynucleotide sequence.

5. A method of transformation of a plant cell with a selected DNA, comprising: transforming the plant cell with the selected DNA, wherein the plant cell comprises a polynucleotide sequence that encodes a sequence complementary to all or part of an XRCC4 mRNA, wherein said polynucleotide sequence suppresses expression of XRCC4 in the plant cell.

6. The method of claim 5, wherein transforming the cell comprises contacting the cell with an *Agrobacterium* cell, or a cell of another member of the Rhizobacteriaceae that comprises the selected DNA.

7. The method of claim 5, wherein the cell is transformed with the selected DNA simultaneously with or subsequent to transforming the cell with the sequence that suppresses the expression of XRCC4.

8. The method of claim 7, wherein the selected DNA comprises a marker gene.

9. The method of claim 5, wherein XRCC4 is stably suppressed.

10. The method of claim 5, wherein XRCC4 is transiently suppressed.

11. The method of claim 5, wherein the plant cell is a dicot cell.

12. The method of claim 11, wherein the dicot cell is a cotton, soybean, rapeseed, sunflower, tobacco, sugarbeet, or alfalfa cell.

13. The method of claim 5, wherein the plant cell is a monocot cell.

14. The method of claim 13, wherein the monocot cell is a corn, rice, wheat, sorghum, barley, oat, switchgrass, or turfgrass cell.

15. The method of claim 5, further comprising treating the cell with a DNA damaging agent before or during transformation.

16. The method of claim 15, wherein the DNA damaging agent induces double strand breaks in the cell genome.

17. The method of claim 15, wherein the DNA damaging agent is bleomycin.

18. A method of transforming a plant cell comprising:
    a) obtaining the plant cell, wherein the plant cell is susceptible to *Agrobacterium*-mediated transformation; and
    b) transforming the plant cell with a selected DNA comprising a polynucleotide sequence that suppresses expression of XRCC4 in the plant by *Agrobacterium*-mediated transformation, wherein the polynucleotide encodes a sequence complementary to all or part of the XRCC4 mRNA, wherein the plant cell expresses the polynucleotide sequence, wherein efficiency of transformation is increased relative to a cell of the same genotype not expressing the polynucleotide sequence.

19. The method of claim 18, wherein the plant cell is a dicot cell.

20. The method of claim 19, wherein the dicot cell is a cotton, soybean, rapeseed, sunflower, tobacco, sugarbeet, or alfalfa cell.

21. The method of claim 18 wherein the plant cell is a monocot cell.

22. The method of claim 21, wherein the monocot cell is a corn, rice, wheat, sorghum, barley, oat, switchgrass, or turfgrass cell.

\* \* \* \* \*